(12) United States Patent
Jensen et al.

(10) Patent No.: US 7,892,794 B2
(45) Date of Patent: Feb. 22, 2011

(54) METHOD, CHIP, DEVICE AND INTEGRATED SYSTEM FOR DETECTION BIOLOGICAL PARTICLES

(75) Inventors: Gert Bolander Jensen, Copenhagen (DK); Lars Thomsen, Ålborg (DK); Oene Robert Veltman, Ålborg (DK)

(73) Assignee: Delta, Dansk Elektronik, Lys & Akustik, Hørsholm (DK)

( * ) Notice: Subject to any disclaimer, the term of this patent is extended or adjusted under 35 U.S.C. 154(b) by 130 days.

(21) Appl. No.: 10/590,632

(22) PCT Filed: Feb. 25, 2005

(86) PCT No.: PCT/DK2005/000130

§ 371 (c)(1),
(2), (4) Date: Nov. 16, 2007

(87) PCT Pub. No.: WO2005/083426

PCT Pub. Date: Sep. 9, 2005

(65) Prior Publication Data

US 2008/0220414 A1 Sep. 11, 2008

(30) Foreign Application Priority Data

Feb. 26, 2004 (DK) ................. 2004 00303

(51) Int. Cl.
*C12Q 1/68* (2006.01)
*C12P 19/34* (2006.01)
*C12M 1/00* (2006.01)
*C12M 1/42* (2006.01)

(52) U.S. Cl. .............. 435/91.2; 435/6; 435/91.1; 435/285.1; 435/285.2

(58) Field of Classification Search .............. None
See application file for complete search history.

(56) References Cited

U.S. PATENT DOCUMENTS

| 342,548 A | 5/1886 | Walker |
| 895,729 A | 8/1908 | Cottrell |
| 1,204,907 A | 11/1916 | Schmidt |
| 1,250,088 A | 12/1917 | Burns |
| 1,605,648 A | 11/1926 | Cooke |

(Continued)

FOREIGN PATENT DOCUMENTS

DE 27 56 164 A1 6/1979

(Continued)

OTHER PUBLICATIONS

Huang et al., "MEMS-based sample preparation for molecular diagnostics," Analytical Bioanal. Chemistry, 2002, vol. 372, pp. 49-65.*

(Continued)

*Primary Examiner*—Young J Kim
(74) *Attorney, Agent, or Firm*—Peter B. Scull; K. Kalan; Berenbaum Weinshienk PC

(57) ABSTRACT

The present invention relates to a method, a chip, a device, and a system for detection of biological particles. The method of the invention typically comprises collecting the biological particles from a gaseous sample, contacting the biological particles with a first liquid reagent, extracting biological material from the collected biological particles, and analyzing the biological material for the presence of a target nucleic acid sequence.

18 Claims, 13 Drawing Sheets

U.S. PATENT DOCUMENTS

| | | | |
|---|---|---|---|
| 1,931,436 | A | 10/1933 | Deutsch |
| 2,085,349 | A | 6/1937 | Wintermute |
| 2,129,783 | A | 9/1938 | Penney |
| 2,142,129 | A | 1/1939 | Hoss et al. |
| 2,297,601 | A | 9/1942 | Williams |
| 2,847,082 | A | 8/1958 | Roos |
| 3,910,779 | A | 10/1975 | Penney |
| 3,999,964 | A | 12/1976 | Carr |
| 4,683,195 | A | 7/1987 | Mullis et al. |
| 4,683,202 | A | 7/1987 | Mullis |
| 4,800,159 | A | 1/1989 | Mullis et al. |
| 4,965,188 | A | 10/1990 | Mullis et al. |
| 4,970,154 | A | 11/1990 | Chang |
| 5,674,742 | A | 10/1997 | Northrup et al. |
| 5,723,591 | A | 3/1998 | Livak et al. |
| 5,891,694 | A | 4/1999 | Arisawa et al. |
| 5,989,824 | A * | 11/1999 | Birmingham et al. .......... 435/6 |
| 6,126,800 | A | 10/2000 | Caillat et al. |
| 6,364,941 | B2 | 4/2002 | Liu et al. |
| 6,511,831 | B1 | 1/2003 | Bernhagen et al. |
| 6,586,253 | B1 | 7/2003 | Harrison et al. |
| 6,623,544 | B1 | 9/2003 | Kaura |
| 6,673,621 | B1 | 1/2004 | Mitchell |
| 2001/0029793 | A1 | 10/2001 | Moler et al. |
| 2002/0017195 | A1 | 2/2002 | Tolvanen |
| 2002/0115201 | A1 | 8/2002 | Barenburg et al. |
| 2003/0136205 | A1 | 7/2003 | Totoki |
| 2003/0146100 | A1 | 8/2003 | Huang et al. |

FOREIGN PATENT DOCUMENTS

| | | |
|---|---|---|
| EP | 1 481 083 B1 | 12/2006 |
| GB | 2329633 A | 3/1999 |
| WO | WO8903426 A2 | 4/1989 |
| WO | WO9708293 A1 | 3/1997 |
| WO | WO9928742 A1 | 6/1999 |
| WO | WO9938612 A1 | 8/1999 |
| WO | WO9957314 A1 | 11/1999 |
| WO | WO 00/26405 A1 | 5/2000 |
| WO | WO0119963 A2 | 3/2001 |
| WO | WO 03/004996 A2 | 1/2003 |
| WO | WO 03/031067 A1 | 4/2003 |
| WO | WO 03/074731 A2 | 9/2003 |
| WO | WO2004/009840 A1 | 1/2004 |
| WO | WO 2004/013329 A1 | 2/2004 |

OTHER PUBLICATIONS

Brown, K. L. 1994. Spore resistance and ultra heat treatment processes. *Journal of Applied Bacteriology Symposium Supplement*, 76:67S-80S.

Lee, et al. 1987. Electrical injury mechanisms: Electrical breakdown of cell membranes. *Plastic and Reconstructive Surgery*, 80(5):672-679.

Riley, R. L. 1974. Airborne infection. *The American Journal of Medicine*, 57:466-475.

Atrih, et al. 2001. Analysis of the role of bacterial endospore cortex structure in resistance properties and demonstration of its conservation amongst species. *Journal of Applied Microbiology*, 91:364-372.

Cano, et al. 1995. Revival and identification of bacterial spores in 25- to 40-million-year-old Dominican amber. *Science*, 268:1060-1064.

Chen, et al. 2000. Analysis of DNA fragments by microchip electrophoresis fabricated on poly(methyl methacrylate) substrates using a wire-imprinting method. *Electrophoresis*, 21:165-170.

Cho, et al. 1999. Kinetics of inactivation of *Bacillus subtilis* spores by continuous or intermittent Ohmic and conventional heating. *Biotechnology and Bioengineering*, 62(3):368-372.

Cserhalmi, et al. 2002. Inactivation of *Saccharomyces cerevisiae* and *Bacillus cereus* by pulsed electric fields technology. *Innovative Food Science & Emerging Technologies*, 3:41-45.

Daniel, et al. 1998. Silicon microchambers for DNA amplification. *Sensors and Actuators A*, 71:81-88.

Dull, et al. 2002. *Bacillus anthracis* aerosolization associated with a contaminated mail sorting machine. *Emerging Infectious Diseases*, 8(10):1044-1047.

Fridez, et al. 1996. PCR DNA typing of stamps: Evaluation of the DNA extraction. *Forensic Science International*, 78:103-110.

Grahl, et al. 1996. Killing of microorganisms by pulsed electric fields. *Appl. Microbiol. Biotechnol.*, 45:148-157.

Iversen, et al. 1975. Electrostatic air filters for dental practice. *Nor Tannlaegeforen Tid*, 85:446-448.

Johns, et al. 1994. Improved methods for the detection of *Bacillus anthracis* spores by the polymerase chain reaction. *Letters in Applied Microbiology*, 18:236-238.

Johnson, et al. 2001. Development of a fully integrated analysis system for ions based on ion-selective optodes and centrifugal microfluidics. *Anal. Chem.*, 73:3940-3946.

Kopp, et al. 1998. Chemical amplication: Continuous-flow PCR on a chip. *Science*, 280:1046-1048.

Lado, et al. 2002. Alternative food-preservation technologies: Efficacy and mechanisms. *Microbes and Infection*, 4:433-440.

Lagally, et al. 2001. Single-molecule DNA amplification and analysis in an integrated microfluidic device. *Analytical Chemistry*, 73: 565-570.

Levi, et al. 2003. Molecular detection of anthrax spores on animal fibres. *Letters in Applied Microbiology*, 36:418-422.

Mafart, et al. 1997. Modelling the heat stress and the recovery of bacterial spores. *International Journal of Food Microbiology*, 37:131-135.

Mainelis, et al. 1999. Collection of airborne microorganisms by electrostatic precipitation. *Aerosol Science and Technology*, 30:127-144.

Mainelis, et al. 2002a. Collection of airborne microorganisms by a new electrostatic precipitator. *Journal of Aerosol Science*, 33:1417-1432.

Mainelis, et al. 2002b. Design and collection efficiency of a new electrostatic precipitator for bioaerosol collection. *Aerosol Science & Technology*, 36(11):1073-1085.

Mainelis, et al. 2002c. Effect of electrical charges and fields on injury and viability of airborne bacteria. *Biotechnology and Bioengineering*, 79(2):229-241.

Mainelis, et al. 2003. Application of electrostatic precipitation for simultaneous determination of culturable and total airborne microorganisms. *American Society for Microbiology General Meeting*, Meeting Abstract, May 18-22, 2003.

Northrup, et al. 1998. A miniature analytical instrument for nucleic acids based in micromachined silicon reaction chambers. *Analytical Chemistry*, 70(5):918-922.

Pugmire, et al. 2002. Surface characterization of laser-ablated polymers used for microfluidics. *Analytical Chemistry*, 74(4):871-878.

Schafer, et al. 2003. Rapid detection and determination of the aerodynamic size range of airborne mycobacteria associated with whirlpools. *Applied Occupational and Environmental Hygiene*, 18(1):41-50.

Schneegaβ, et al. 2001. Miniaturized flow-through PCR with different template types in a silicon chip thermocycler. *Lab on a Chip*, 1:42-49.

Shoffner, et al. 1996. Chip PCR. I. Surface passivation of microfabricated silicon-glass chips for PCR. *Nucleic Acids Research*, 24(2):375-379.

Spilimbergo, et al. 2003. Inactivation of bacteria and spores by pulse electric field and high pressure $CO_2$ at low temperature. *Biotechnology and Bioengineeringing*, 82(1):118-125.

Sung, et al. 2001. Plastic microchip electrophoresis for genetic screening: The analysis of polymerase chain reactions products of fragile X (CGG)n alleles. *Electrophoresis*, 22:1188-1193.

Tsong, T. Y. 1991. Electroporation of cell membranes. *Biophysical Journal*, 60:297-306.

Tsong, et al. 1999. Biological effects of electric shock and heat denaturation and oxidation of molecules, membranes, and cellular functions. *Annals New York Academy of Sciences*, 888:211-232.

Vincent, et al. 1999. Application of recent advances in aerosol sampling science towards the development of improved sampling devices: The way ahead. *J. Environ. Monit.*, 1:285-292.

International Search Report dated Aug. 19, 2005 for PCT/DK2005/000130.

International Preliminary Report on Patentability dated Mar. 20, 2006 for PCT/DK2005/000130.

Co-pending U.S. Appl. No. 10/590,630, filed Aug. 23, 2006, titled Method, Chip, Device and System for Extraction of Biological Materials.

Co-pending U.S. Appl. No. 10/590,648, filed Aug. 23, 2006, titled Method, Kit and System for Enhanced Nested PCR.

Co-pending U.S. Appl. No. 10/590,768, filed Aug. 24, 2006, titled Method, Chip, Device and System for Collection of Biological Particles.

Boe et al., Replication Origins of Single-Stranded-DNA Plasmid pUB110, Journal of Bacteriology, Jun. 1989, p. 3366-3372, vol. 171, No. 6.

O'Brien et al., Size and Concentration Measurement of an Industrial Aerosol, Am.Ind.Hyg.Assoc.J, 1986, p. 386-392, vol. 47(7).

Pappaert, K. et al., Diffusion-Reaction Modelling of DNA Hybridization Kinetics on Biochips, Chemical Engineering Science, 2003, pp. 4921-4930, vol. 58, Elsevier Ltd.

Lee, Sang-Wook, et al., "A Micro Cell Lysis Device," Sensors and Actuators; 1999; vol. 73, pp. 74-79; Elsevier Science S.A.

Cheng, Jing, et al., "Isolation of Cultured Cervical Carcinoma Cells Mixed with Peripheral Blood Cells on a Bioelectronic Chip," Analytical Chemistry; 1998; vol. 70, pp. 2321-2326; American Chemical Society.

International Search Report dated Jun. 14, 2005 for PCT/DK2005/000132.

International Preliminary Report on Patentability dated Feb. 6, 2006 for PCT/DK2005/000132.

International Search Report dated Aug. 17, 2005 for PCT/DK2005/000133.

International Preliminary Report on Patentability dated Feb. 6, 2006 for PCT/DK2005/000133.

\* cited by examiner

METHOD, CHIP, DEVICE AND INTEGRATED SYSTEM FOR DETECTION BIOLOGICAL PARTICLES

CROSS REFERENCE TO RELATED APPLICATION

This application is a U.S. National Phase of PCT International Application Number PCT/DK2005/000130, filed on Feb. 25, 2005, designating the United States of America and published in the English language, which claims priority under 35 U.S.C. §119 to Denmark Application Number PA 2004 00303 filed on Feb. 26, 2004. The disclosures of the above-described applications are hereby incorporated by reference in their entirety.

FIELD OF THE INVENTION

The present invention relates to a method, a chip, a device and a system for detection of biological particles. Method of the invention typically comprises collecting the biological particles from a gaseous sample, contacting the biological particles with a first liquid reagent, extracting biological material from the collected biological particles, and analysing the biological material for the presence of a target nucleic acid sequence.

BACKGROUND

In order to facilitate rapid detection of airborne pathogens capable of causing either natural or deliberate epidemics it is important to collect particles that holds or consists of the said pathogens in order to facilitate rapid detection. Diseases that are spreading through air pose a serious health risk to man. According to the World Health Organization (WHO) as many as 1000 million people may become infected with Tuberculosis between 2002 and 2020, of which approximately 150 million will get sick and 36 million people will die from the disease. The first new communicable airborne disease of the 21st century is Severe Acute Respiratory Syndrome (SARS), which has the potential of generating rapidly spreading infections. Parallels can be feared with the spread of the Plague ("the Black Death") with Europe's Middle Ages, when approximately 25 million people died in the period 1347 to 1352. The most deadly form of the Plague is by inhalation of infectious aerosols, where as little as 1-10 cells of *Yersinia pestis* are sufficient to cause disease. The aerosols can arise by respiration of infected humans or, more threateningly, from deliberate releases *Y. pestis* by bioterrorists.

Biological warfare (BW) agents of critical concern are bacterial spores, such as *Bacillus anthracis* (anthrax), *Clostridium tetani* (tetanus), and *Clostridium botulinum* (botulism). Spores, produced by certain types of Gram-positive bacteria in response to starvation, are non-growing, heat-resistant, dehydrated, and resistant to extremes of temperature, pH, desiccation, radiation, and chemical agents. This stability makes them an attractive tool for use in BW weapons.

Other micro-organisms with the potential of being used to generate deliberate epidemics comprises micro-organisms causing e.g., Smallpox, Ebola, Encephalitis, and Q-fever. Also feared are the natural occurring recombination products of airborne influenza with the deadly Avian flu. These recombined viruses have the potential of causing pandemics facilitated by air travel of as of yet unseen dimensions.

U.S. Pat. No. 5,674,742 discloses an integrated microfabricated instrument for manipulation, reaction and detection of microliter to picoliter samples. The instrument is suited for biochemical reactions, particularly DNA-based reactions such as the polymerase chain reaction, that require thermal cycling since the inherently small size of the instrument facilitates rapid cycle times. The integrated nature of the instrument provides accurate, contamination-free processing. The instrument may include reagent reservoirs, agitators and mixers, heaters, pumps, and optical or electromechanical sensors. Ultrasonic Lamb-wave devices may be used as sensors, pumps and agitators.

U.S. Pat. No. 6,586,253 discloses a method for the detection of cell contents which contains the steps of, introducing a cell into a channel in a microchip; lysing the cell to release cell contents into the channel; moving the cell contents towards a detection zone; and detecting the cell contents at the detection zone. An apparatus for the detection of cell contents is furthermore disclosed, the apparatus comprising: a microchip; a cell mobilization channel formed in the microchip, the cell mobilization channel having a cell introduction end and a detection end; a cell mobilizer operably connected with the cell introduction end for moving cells from the cell introduction end to the detection end; means for lysing cells in the cell mobilization channel at a lysing zone, the lysing zone being located between the cell introduction end and the detection end; and a detector, disposed adjacent the detector end, arranged to detect cell contents appearing at the detector end that have been moved from the lysing zone to the detector end by the cell mobilizer.

U.S. Pat. No. 6,673,621 discloses a device suitable for marking a collected sample, comprising collecting means for collecting the sample and at least one detectable marker which is associated with at least a portion of the collecting means, wherein the at least one detectable marker is contractable with the sample upon collection of the sample to mark the collected sample upon contact of the sample with the at least a portion of the collecting means having the at least one detectable marker associated therewith, and wherein the at least one detectable marker is other than a component which is present in the sample before collection and is inert to any component present in the sample before collection. It furthermore discloses kits containing the device, methods for marking samples using the device, methods for determining the integrity of a marked sample, and use of the markers for the testing of laboratories and/or laboratory personnel for certification, proficiency testing or accreditation purposes are also provided.

SUMMARY OF THE INVENTION

An object of the present invention relates to a provision of a method, a chip, a device and a system for performing rapid detection of biological particles.

Another object of the present invention relates to a provision of a method, a chip, a device and a system for performing sensitive detection of biological particles.

Yet another object of the present invention relates to a provision of a method, a chip, a device and a system suitable for performing decentralised, and preferably fully automated, detection of biological particles.

Still another object of the present invention relates to a provision of a method, a chip, a device and a system for performing detection of biological particles with a minimum of manual sample handling.

Still another object of the present invention relates to a provision of a method, a chip, a device and a system for performing detection of biological particles, the method, chip, device and system using a minimum of energy for the detection.

Thus, an object of the present invention relates to the provision of direct collection of biological particles from gaseous samples such as air samples.

Another object of the present invention relates to the provision of methods, chips, devices and systems for up-concentrating biological particles from a large gaseous sample into a much smaller volume, i.e. increasing the concentration of the biological particles.

Yet another object of the present invention relates to the provision of methods, chips, devices and systems in which collection and up-concentration of the biological particles are performed in the same structure and preferably also in the same step.

Still another object of the present invention relates to the provision of methods, chips, devices and systems that easily allows for further analysis of collected biological particles.

A further object of the present invention relates to the provision of methods, chips, devices and systems that easily allows for further analysis of collected biological particles.

Also, an object of the invention relates to the provision of methods, chips, devices and systems that collect biological particles with high capture efficiency.

Other objects of the invention will become apparent when reading the description and the examples.

An aspect of the present invention relates to a method for detecting a biological particle from a gaseous sample, the method comprising the steps of:
  a) providing a sample chamber and a first and a second electrode, the first and the second electrode and the sample chamber being so positioned that at least a part of the sample chamber is between the first and the second electrode, a distance between the first and the second electrode being at most 20 mm,
  b) providing a gaseous sample in the sample chamber,
  c) applying an first potential to the first electrode and a second potential to the second electrode, thus resulting in a potential difference and an electric field between the first and second electrode, to assist electrostatic collection, in the sample chamber, of a biological particle from the gaseous sample,
  d) contacting the collected biological particle with a first liquid reagent, thus obtaining a reaction mixture,
  e) exposing said reaction mixture to an alternating electric field in said sample chamber, said alternating electric field having a sufficient amplitude to extract biological material of the biological particle,
  f) performing nucleic acid amplification of a target nucleic acid sequence, and
  g) measuring the presence of the amplified target nucleic acid sequence and/or products resulting from amplification of the target nucleic acid sequence and optionally inferring that the biological particle has been detected in the sample if at least the one copy of amplified target nucleic acid sequence is present and/or if at least one product resulting from amplification of the target nucleic acid sequence is present.

Yet a further aspect of the invention relates to a chip for detecting a biological particle from a gaseous sample, the chip comprising
  a sample chamber, e.g. comprising a first opening in fluid connection with the surrounding air, and
  a second opening to form a fluid connection with a device, the sample chamber comprising a gaseous sample.

An additional aspect of the invention relates to a device for detecting a biological particle from a gaseous sample, the device comprising:
  a chip site where a chip is to be located in order be functionally associated with the device,
  an electrical interface between the device and the chip for applying an alternating electric field between the electrodes of the sample chamber, and
  a programmable unit comprising a software that effects that the device performs one or more actions selected from the group consisting of:
    providing a gaseous sample in sample chamber,
    applying an first potential to the first electrode and a second potential to the second electrode, thus resulting in a potential difference and an electric field between the first and second electrode, to assist electrostatic collection, in the sample chamber, of a biological particle in the gaseous sample,
    contacting the collected biological particle with a first liquid reagent,
    exposing a reaction mixture to an alternating electric field in said sample chamber, said alternating electric field having a sufficient amplitude so as to extract biological material from the biological particle,
    performing nucleic acid amplification of a target nucleic acid sequence, measuring the presence of the amplified target nucleic acid sequence and/or measuring products resulting from amplification of the target nucleic acid sequence.

Yet a further aspect of the invention relates to a system for detecting a biological particle from a gaseous sample, the system comprising a chip as defined herein functionally associated with a device as defined herein.

BRIEF DESCRIPTION OF THE FIGURES

In the following some embodiments of the present invention will be described with reference to the figures, wherein.

DETAILED DESCRIPTION OF THE INVENTION

Figure 1:
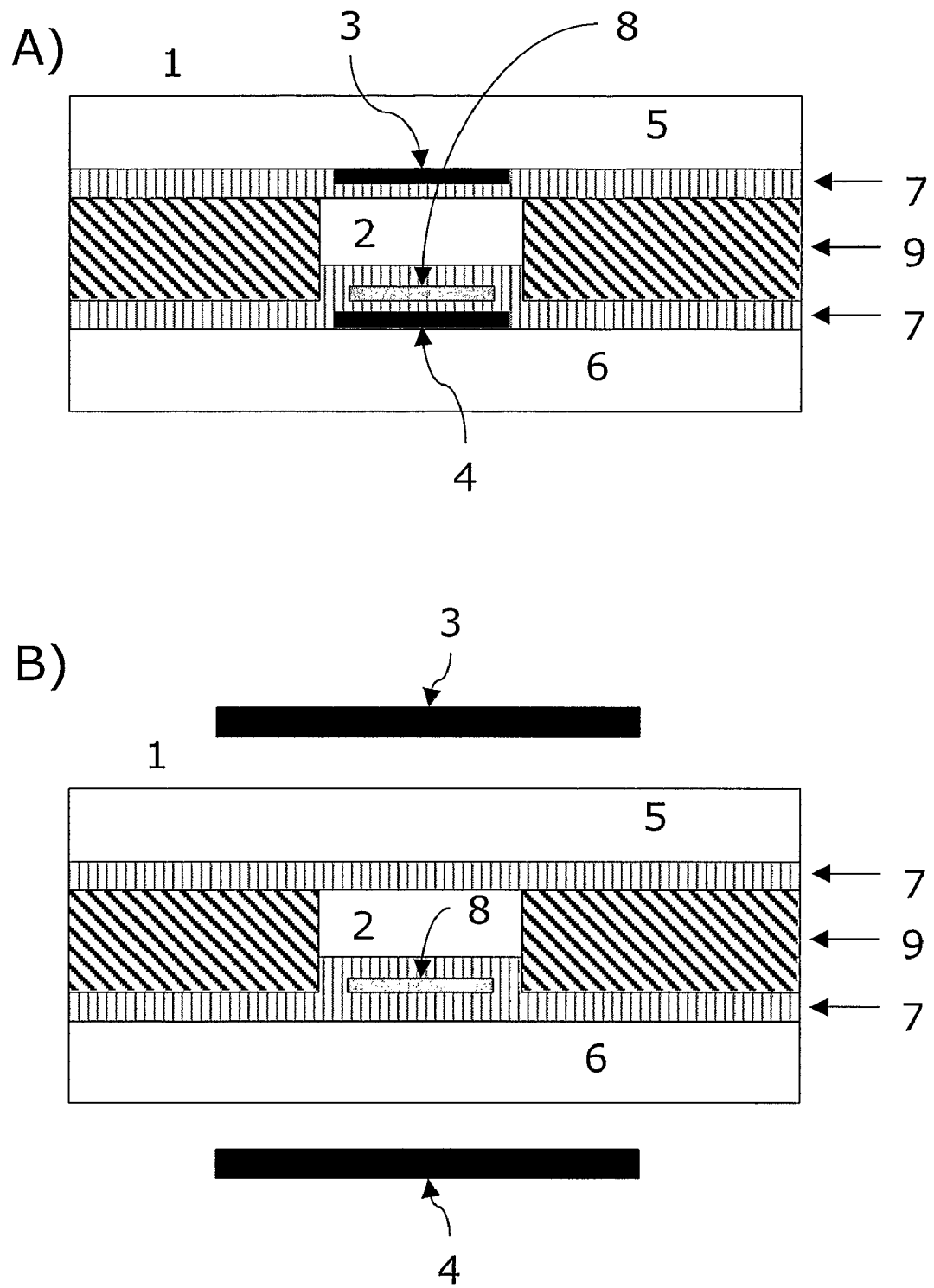
FIG. 1 illustrates the cross section of two exemplary embodiments of the chip.

An aspect of the present invention relates to a method for detecting a biological particle from a gaseous sample, the method comprising the steps of:
  a) providing a sample chamber and a first and a second electrode, the first and the second electrode and the sample chamber being so positioned that at least a part of the sample chamber is between the first and the second electrode, a distance between the first and the second electrode being at most 20 mm,
  b) providing a gaseous sample in the sample chamber, c) applying an first potential to the first electrode and a second potential to the second electrode, thus resulting in a potential difference and an electric field between the first and second electrode, to assist electrostatic collection, in the sample chamber, of a biological particle from the gaseous sample, d) contacting the collected biological particle with a first liquid reagent, thus obtaining a reaction mixture, e) exposing said reaction mixture to an alternating electric field in said sample chamber, said alternating electric field having a sufficient amplitude to extract biological material of the biological particle, f) performing nucleic acid amplification of a target nucleic acid sequence, and g) measuring the presence of the amplified target nucleic acid sequence and/or products resulting from amplification of the target nucleic acid sequence and optionally inferring that the biological particle has been detected in the sample if at least the one copy of amplified target nucleic acid sequence is present and/or if at least one product resulting from amplification of the target nucleic acid sequence is present.

According to the present invention the term "biological particle" is related to a particle comprising e.g. a microorganism and/or a virus and/or a fragment thereof.

The term "and/or" used in the context "X and/or Y" should be interpreted as "X", or "Y", or "X and Y".

The microorganism may e.g. be selected from the group consisting of an archeal microorganism, a eubacterial microorganism or a eukaryotic microorganism.

E.g., the microorganism may be selected from the group consisting of a bacterium, a bacterial spore, a virus, a fungus, and a fungal spore.

In a preferred embodiment of the invention, the microorganism is an airborne microorganism.

The biological particle may also comprise a plant spore or a fragment thereof.

In a preferred embodiment of the invention, the microorganism is a bacterial spore.

For example, the bacterial spore may be formed by a bacterium selected from the genus *Bacillus* and/or the genus *Clostridium*.

In a preferred embodiment of the invention, the bacterial spore is a spore formed by *Bacillus anthracis*. The biological particle may e.g. comprise a bacterial spore formed by *Bacillus anthracis*. Also, the biological particle may essentially consist of one or more bacterial spores formed by *Bacillus anthracis*.

The term "gaseous sample" relates to a sample comprising one or more gasses and possibly also biological particles. The gaseous sample may e.g. be an air sample, such as environmental samples of air, sample of air resulting from a vaccum suction of powdered materials like earth, sand, dust or unidentified powder. The gaseous sample to be examined may originate from a person exhaling a breath sample containing or susceptible to contain microorganisms.

According to the present invention the terms "sample chamber", "container" and "reaction chamber" are used interchangeably.

In a preferred embodiment of the invention, the sample chamber is comprised by a chip, that is to say, a cartridge or a biochip. The sample chamber may e.g. be comprised by a chip as defined herein.

In a preferred embodiment, the first and second electrodes are positioned at opposing sides of the sample chamber.

In an embodiment of the invention, the first and/or second electrodes have a substantial form selected from the group consisting of a sheet, a plate, a disc, a wire, a rod, or any combination thereof. It is presently preferred that at least one electrode has a sheet form and it is even more preferred that both the first and the second electrode have sheet-forms.

In an embodiment of the invention, the first and a second electrode are separated by a distance being at the most 20 mm, preferably being at the most 20 mm, such as at most 15 mm, 10 mm, 9 mm, 8 mm, 7 mm, 6 mm, 5 mm, or at most 4 mm, more preferably being at the most 3 mm, and even more preferably at most 0.5 mm such as at most 0.3 mm, 0.2 mm, 0.1 mm, such as at most 0.05 mm.

For example the first and the second electrode may be separated by a distance in the range of 0.05-20 mm, such as in the range of 0.05-0.1, 0.1-0.2, 0.2-0.3, 0.3-0.4, 0.4-0.5, 0.5-1, 1-2, 2-5, 5-10, or 10-15 mm, such as in the range of 15-20 mm.

Typically the first and the second electrode may be separated by a distance, which is at least 0.02 mm such as at least 0.03 mm or 0.05 mm.

In step c), one or more biological particles are collected from the gaseous sample. The collection of biological particles may be performed according to the method and using the chip, device and system described in the co-pending PCT application "Method, chip, device and system for collection of biological particles" having the application Ser. No. PCT/DK2005/000133 (WO2005/083391 A1), which is incorporated herein by reference.

In an embodiment of the invention, the biological particles are collected from the gaseous sample while the gaseous sample is flowing through the sample chamber. In another embodiment, the biological particles are collected from the gaseous sample while the gaseous sample is recirculated through the sample chamber, i.e. the gaseous sample passes through the sample chamber more than one time, in order to enhance the capture efficiency. For example, when recirculated, the gaseous sample may flow through the sample chamber at least 2 times, 3 times, 4 times, 5 times, 10 times, 15 times, 20 times, 30 times, 40 times, 50 times, or 75 times, such as at least 100 times. The gaseous sample may e.g. flow through the sample a number of times in the range of 2-200, such as 2-50 times, 50-100 times or 100-200 times.

In an embodiment of the invention, the gaseous sample is provided in the sample chamber by means of a gas flow. During the collection of biological particles the gas flow typically has a flow rate ranging preferably from about 5-1000 mL/minute.

In an embodiment of the invention, the gas flow has been terminated before the biological particles are collected from the gaseous sample.

Normally, at least a part of the gaseous sample in sample chamber is positioned or flows between the first and the second electrode. For example, at least 40% of the volume of the gaseous sample is positioned or flows between the first and the second electrode, such as at least 50, 60, 70, 80, 90, 95, 97.5, 99, 99.5, or 99.9% of the volume of the gaseous sample is positioned or flows between the first and the second electrode, such as at least 100% of the volume of the gaseous sample is positioned or flows between the first and the second electrode.

In yet an embodiment of the invention, the electric field of the first and the second electrode are selected so at yield a capture efficiency of at least 50% for biological particles having an effective length in the interval from 1-10 micrometer.

The electric field magnitude may be chosen from the group of: 50 V/mm, 100 V/mm, 200 V/mm, 300 V/mm, 400 V/mm, 500 V/mm, 600 V/mm, 700 V/mm, 800 V/mm, 900 V/mm, 1000 V/mm, 1100 V/mm, 1200 V/mm, 1300 V/mm, 1400 V/mm, 1500 V/mm, 1600 V/mm, 1700 V/mm, 1800 V/mm, 1900 V/mm, 2000 V/mm.

For example the electric field magnitude may be in the range of 50-2000 V/mm, such as in the range of 50-100, 100-200, 200-300, 300-400, 400-500, 500-750, 750-1000, 1000-1200 V/mm, 1200-1500 V/mm, such as in the range of 1500-2000 V/mm.

In a preferred embodiment of the invention, the first and second electrode are respectively negatively charged and positively charged, or vice versa. For example, if the potential difference between the two electrodes are the 400 V, the negatively charged electrode may have a potential of −200 V relative to ground and the positively charged electrode may have a potential of 200 V relative to ground.

In a highly preferred embodiment of the invention, the first potential of the first electrode and the second potential of the second electrode, and thus the electric field between the first and the second electrode, are selected so as to yield a capture efficiency of at least 50% for biological particles having an effective length in the interval from 1-10 micrometer, such as a capture efficiency of at least 70%, preferably at least 80%, and more preferably at least 90%, such as at least 95%, 97.5%, 99, 99.5 or 99.9% such as approximately 100%.

Preferably, the capture efficiency is determined according to the standardised method of Example 2.

According to the present invention, the term "effective length" of a particle is the aerodynamic diameter of the particle e.g. as measured by laser light scattering (O'Brien et al 1986). The aerodynamic diameter of a particle, $d_{pa}$, may be estimated by the formula $$d_{pa} = d_{ps} \cdot \sqrt{\rho_p}$$

where $d_{ps}$ is Stoke diameter in µm and $\rho_p$ is the particle density in g/cm$^3$.

In a preferred embodiment of the invention, the collected biological particles of the sample chamber are contacted with a first liquid reagent. It may be preferred that the biological particles are contacted while they are still located between the first and the second electrode.

In step d) the collected biological particle are contacted with a first liquid reagent and the resulting mixture is called the reaction mixture.

The first liquid reagent comprises one or more reagents required to perform a nucleic acid amplification.

The first liquid reagent may comprise one or more reagents selected from the group consisting of a primer, a nucleic acid, a triphosphate nucleotide and a nucleic acid polymerase.

The first liquid reagent may furthermore comprise additives such as 2-mercaptoethanol, e.g. in a concentration of 10 mM, BSA e.g. in a concentration of 1 mg/ml and/or a detergent e.g. in a concentration of 0.5% to 6% (w/v). The detergent may be selected from the group consisting of Triton X-100, Triton X-114, NP-40, Tween20, Tween80 and similar non-ionic detergents.

In the present context, the term "nucleic acid", "nucleic acid sequence" or "nucleic acid molecule" should be interpreted broadly and may for example be an oligomer or polymer of ribonucleic acid (RNA) or deoxyribonucleic acid (DNA) or mimetics thereof. This term includes molecules composed of naturally-occurring nucleobases, sugars and covalent internucleoside (backbone) linkages as well as molecules having non-naturally occurring nucleobases, sugars and covalent internucleoside (backbone) linkages which function similarly or combinations thereof. Such modified or substituted nucleic acids may be preferred over native forms because of desirable properties such as, for example, enhanced affinity for nucleic acid target molecule and increased stability in the presence of nucleases and other enzymes, and are in the present context described by the terms "nucleic acid analogues" or "nucleic acid mimics". Preferred examples of nucleic acid mimetics are peptide nucleic acid (PNA-), Locked Nucleic Acid (LNA-), xylo-LNA-, phosphorothioate-, 2'-methoxy-, 2'-methoxyethoxy-, morpholino- and phosphoramidate—comprising molecules or functionally similar nucleic acid derivatives.

The term "nucleic acid polymerase" relates to a DNA- or RNA-dependent DNA polymerase enzyme that preferably is heat stable, i.e., the enzyme catalyzes the formation of primer extension products complementary to a template and does not irreversibly denature when subjected to the elevated temperatures for the time necessary to effect denaturation of double-stranded template nucleic acids. Generally, the synthesis is initiated at the 3' end of each primer and proceeds in the 5' to 3' direction along the template strand. Thermo stable polymerases have been isolated from thermophilic or caldoactive strains such as *Thermus flavus, T. ruber, T. thermophilus, T. aquaticus, T. lacteus, T. rubens, Thermococcus litoralis, Pyrococcus furiosus, Bacillus stearothermophilus* and *Methanothermus fervidus*. Nonetheless, polymerases that are not thermo stable also can be employed in nucleid acid amplification provided the enzyme is replenished.

The first liquid reagent may furthermore comprise a 5'-3' exonuclease degradable, oligo-nucleic acid probe, the degradation of said nucleic acid probe resulting in release of a redox active component.

The redox active component may e.g. be a metallocene such as e.g. ferrocene.

In step e) the reaction mixture is exposed to an alternating electric field. The alternating electric field may be provided by the first and second electrode that provide the electric field for collection or it may be provided by another set of electrodes.

The extraction of biological material may be performed according to the method and using the chip, device and system described in the co-pending PCT application "Method, chip, device and system for extraction of biological material" having the application Ser. No. PCT/DK2005/000132 (WO2005/083078 A1), which application is incorporated herein by reference.

In a preferred embodiment of the invention, the part of the exposed reaction mixture, on which further genetic analysis is performed, comprises at least 20% of the reaction mixture in the sample chamber, such as at least 30, 40, 50, 60, 70, 80, 90, 95, 97.5, 99, 99.5, or 99.9% of the reaction mixture in the sample chamber, such as at least approximately 100% of the reaction mixture in the sample chamber.

According to the present invention, the terms "extraction" and "extracting" relate to releasing biological material of the one or more biological cells, that is e.g. to say, making it for available for further analysis in the reaction mixture. The terms "extraction" and "extracting" are also related to e.g. opening or rupturing the cell wall or cell barrier of the biological particle.

The biological material extracted from the biological particle will typically comprises a component selected from the group consisting of a cell organelle, a genetic material, and a protein.

The genetic material may e.g. comprise chromosomal DNA and/or plasmid DNA and/or any type of RNA.

The protein may e.g. be selected from the group consisting of enzymes, structural proteins, transport proteins, ion channels, toxins, hormones, and receptors.

Preferably, the biological material comprises DNA and/or RNA.

According to the present invention, the term "alternating electric field" relates to electric fields that change over time. The alternating electric field may e.g. be the electric field that occurs from periodically shifting the polarity of two electrodes between positive/negative and negative/positive, i.e. connecting an AC source to the electrodes. The alternating electric field may e.g. comprise or be an AC field. The alternating electric field may e.g. comprise one or more DC pulses.

It is important that the alternating electric field has a sufficient amplitude and is applied for a sufficient duration of time to extract the biological material. It may also be important that the alternating electric field furthermore has a sufficient frequency to extract the biological material.

In a preferred embodiment of the invention, the frequency of the alternating electric field is at the least 5 kHz, preferably being at least 20 kHz, and more preferably being at least 50 kHz.

In another preferred embodiment of the invention, the frequency of the alternating electric field is at the least 100 kHz, preferably being at least 250 kHz, and more preferably being at least 500 kHz.

For example, the frequency of the alternating electric field may be at least 5 kHz, such as at least 10, 20, 50, 100, 200, 300, or 400 kHz, such as at least 500 kHz. Even higher frequencies such as 1000 kHz, 2000 kHs or 5000 kHz is envisioned.

Preferably the frequency of the alternating electric field is at most 750 kHz, such as at most 500 kHz.

Thus, the frequency of the alternating electric field may e.g. be in the range of 5-750 kHz, such as in the range of 5-10, 10-20, 20-50, 50-100, 100-200, 200-300, 300-400, or 400-500 kHz, such as in the range of 500-750 kHz. Preferably, the frequency of the alternating electric field may e.g. be in the range of 60-750 kHz, such as 70-750 kHz, 80-750 kHz, 90-750 kHz, or 100-750 kHz.

The amplitude of the alternating electric field, that is, the maximum potential difference between the first and the second electrode, is typically at most 30 V, such as at most 25, 20, 15, 10, 8, 6, 5, 4, 3, or 2 V, such as at most 1 V.

The amplitude of the alternating electric field, that is, the maximum potential difference between the first and the second electrode, may e.g. be in the range of 1-30 V, such as in the range of 1-2, 2-3, 3-4, 4-5, 5-6, 6-8, 8-10, 10-15, 15-20, or 20-25 V, such as in the range of 25-30 V.

An interesting measure of the extraction of biological material is the DNA/RNA release percentage. The "DNA/RNA release percentage" is percentage of biological cells in the sample chamber that release their DNA and/or RNA due to the exposure in step c) to the alternating electric field. The DNA/RNA release percentage is determined according to the standardised method described in Example 3.

The extraction and thus the DNA/RNA release percentage of biological cells in the sample chamber or in a chip comprising the sample chamber is strongly dependent on the design of and the distance between the first and the second electrode, the structure and materials of the sample chamber and the potentials applied to the first and the second electrode.

In a highly preferred embodiment of the invention, the first potential of the first electrode and the second potential of the second electrode, and thus the alternating electric field between the first and the second electrode, are modulated so as to yield a DNA/RNA release percentage of at least 30%, such as a DNA/RNA release percentage of at least 40%, preferably of at least 50%, and more preferably of at least 60%, such as of at least 70%, 80%, 90%, 95%, 97.5%, 99, 99.5 or 99.9% such as approximately of 100%.

In an another preferred embodiment of the invention, the first potential of the first electrode and the second potential of the second electrode, and thus the alternating electric field between the first and the second electrode, are modulated so as to yield a DNA/RNA release percentage of at least 30% of the bacterial spores in the sample chamber, such as a DNA/RNA release percentage of at least 40%, preferably of at least 50%, and more preferably of at least 60% of the bacterial spores in the sample chamber, such as of at least 70%, 80%, 90%, 95%, 97.5%, 99, 99.5 or 99.9% such as approximately of 100% of bacterial spores in the sample chamber.

In a preferred embodiment, the alternating electric field provided by modulating the polarity of the two electrodes.

The alternating electric field may have a substantial form chosen from the group consisting of: rectangular, sinusoidal, saw-tooth, asymmetrical triangular, symmetric triangular; or any combination thereof.

Also, the alternating electric field, in the frequency domain, may comprise a least a first and a second frequency component.

In an embodiment of the invention, the reaction mixture is exposed to the alternating electric field for at most 3600 seconds, such as at most 3000, 2000, 1000, 500, 250, 100, 50, 40, 30, 20, 10, 5, 4, or 3 seconds, such as at most 1 seconds.

For example, the reaction mixture may be exposed to the alternating electric field in the range of 0.01-3600 seconds, such as in the range of 0.1, 1-5, 5-10, 10-25, 25-50, 50-100, 100-250, 250-500, 500-1000, or 1000-2000 seconds, such as in the range of 2000-3600 seconds.

In a preferred embodiment of the invention, the reaction mixture is exposed to the alternating electric field for at most 250 second, preferably for at most 100 second such as for at most 30 seconds.

Step f) comprises performing a nucleic acid amplification of a target nucleic acid sequence. Preferably, the target nucleic acid sequence is selected to be specific for the biological particle.

According to the present invention, the term "target nucleic acid sequence" (TNAS) relates to a nucleic acid sequence of special interest, e.g. for analytical or diagnostic purposes. The TNAS may e.g. be a gene or a fragment of a gene.

According to the present invention, the term "nucleic acid amplification" relates to a process in which a template, e.g. a fragment of the nucleic acid comprising the TNAS, is copied into a number of copies.

In a preferred embodiment of the invention, the nucleic acid amplification of step f) is performed using an amplification technique selected from the group consisting of Polymerase Chain Reaction techniques (PCR), Strand Displacement Amplification (SDA), Ligation-Rolling Circle Amplification (L-RCA) and their combinations/modifications. These methods as well as PCR are well known to the person skilled in the art and are e.g. described in Sambrook et al.

Preferably, the nucleic acid amplification of step f) is PCR. Polymerase chain reaction (PCR) is one of the most commonly used nucleic acid amplification techniques. U.S. Pat. Nos. 4,683,202, 4,683,195, 4,800,159, and 4,965,188 disclose embodiments of the PCR technique. PCR typically employs two oligonucleotide primers that bind to a selected nucleic acid template (e.g., DNA or RNA). A primer can be purified from a restriction digest by conventional methods, or it can be produced synthetically. The primer is preferably single-stranded for maximum efficiency in amplification, but the primer can be double-stranded. Double-stranded primers are first denatured, i.e., treated to separate the strands. One method of denaturing double stranded nucleic acids is by heating.

After the double-stranded nucleic acid is denatured by heat, the reaction mixture is allowed to cool to a temperature that promotes annealing of each primer the nucleic acid sequence comprising the TNAS. The temperature for annealing is usually from about 35° C. to about 65° C. The annealing time is typically from about 1 second to about 1 min. The reaction mixture is then adjusted to a temperature at which the activity of the polymerase is promoted or optimized, i.e., a temperature sufficient for extension to occur from the annealed primer to generate products complementary to the template nucleic acid. The temperature should be sufficient to synthesize an extension product from each primer that is annealed to a nucleic acid template, but should not be so high as to denature an extension product from its complementary template (e.g., the temperature for extension generally ranges from about 40° C. to 80° C.). The extension time is normally from about 5 seconds (in lab-on-chip settings) to about 5 minutes.

According to the present invention, the term "primer" relates to a nucleic acid sequence, which is capable of hybridising e.g. to the TNAS, to a nucleic acid sequence in the vicinity of the target sequence, or to a nucleic acid sequence overlapping with the TNAS. Alternatively, a primer may be capable of hybridising to either the complementary sequence of the TNAS, to the complementary sequence of a nucleic acid sequence in the vicinity of the TNAS, or to the complementary sequence of a nucleic acid sequence overlapping with the TNAS.

The primers typically comprise oligonucleotides, that is, nucleic acid molecules comprising in the range of 5-30 nucleotides, such as in the range of 5-10 nucleotides, 10-15 nucleotides, 15-20 nucleotides, 20-25 nucleotides, and 25-30 nucleotides. It is also envisioned that longer nucleic acid molecules may be used as primers. Thus, a primer may comprise a nucleic acid molecule comprising in the range of 30-50 nucleotides, such as in the range of 30-35 nucleotides, 35-40 nucleotides, 40-45 nucleotides, and 45-50 nucleotides.

For example, a primer may essentially consist of an oligonucleotide, that is, nucleic acid molecules essentially consisting of in the range of 5-30 nucleotides, such as in the range of 5-10 nucleotides, 10-15 nucleotides, 15-20 nucleotides, 20-25 nucleotides, and 25-30 nucleotides. Also, a primer may be a nucleic acid molecule essentially consisting of in the range of 30-50 nucleotides, such as in the range of 30-35 nucleotides, 35-40 nucleotides, 40-45 nucleotides, and 45-50 nucleotides.

It is especially preferred that the nucleic acid amplification of step f) is nested PCR. Nested PCR uses at least two pairs of primers, that is, a pair of outer primers and a pair of inner primers. In a pair of primers, one primer, the sense primer, is typically designed to be capable of hybridising to the nucleic acid strand comprising the TNAS strand. The other primer, the antisense primer, is typically designed to be capable of hybridising to the complementary nucleic acid strand of the nucleic acid strand comprising the TNAS strand. First a PCR process involving the outer pair of primers are performed, thereby enriching the reaction mixture with nucleic acid molecules comprising the TNAS or fragments thereof and reducing the noise from other nucleic acid sequences of the reaction mixture. Next, a PCR process involving the inner pair of primers are performed, thus specifically amplifying the TNAS or a fragment thereof.

It is even more preferred to perform a nested PCR in a single-tube format, that is, nested PCR where both the outer pair of primers and the inner pair of primers are present in the reaction mixture at the same time. One major advantage of using single-tube nested PCR in the context of automated and e.g. chip based detection systems is that the complexity of the liquid handling is dramatically reduced in comparison to conventional nested PCR where the outer and inner pair of primers have to be added into the reaction mixture sequentially.

Typically, the melting temperature (Tm) of the pair of outer primers is at least 2° C. higher than the Tm of the pair of inner primers. This difference in Tm makes it possible to perform the PCR process exclusively with the outer pair of primers by keeping the annealing temperature higher than the Tm for the inner pair of primers. The PCR process involving the inner pair of primers is initiated by reducing the annealing temperature below the Tm of the inner pair of primers.

For example, Single-tube nested PCR may e.g. be performed by the method comprising the steps of:
 i) cycling, at least two times, the temperature of the reaction mixture between a first denaturation temperature, a first annealing temperature and a first extension temperature, the first annealing temperature being similar to or lower than the lowest Tm of the outer primer pair and higher than the highest Tm of the inner primer pair, and
 ii) cycling, at least two times, the temperature of the reaction mixture between a second denaturation temperature, a second annealing temperature and a second extension temperature, the second annealing temperature being similar to or lower than the lowest Tm of the inner primer pair The single-tube nested PCR process and the detection may e.g. be performed according to the methods and using the kits described in the co-pending PCT application "Method, kit and system for enhanced Nested PCR" having the application Ser. No. PCT/DK2005/000131 (WO2005/083114 A1), which is incorporated herein by reference.

Step g) involves measuring the presence of the amplified target nucleic acid sequence and/or products resulting from amplification of the target nucleic acid sequence and optionally inferring that the biological particle has been detected in the sample if at least the one copy of amplified target nucleic acid sequence is present and/or if at least one product resulting from amplification of the target nucleic acid sequence is present.

In a preferred embodiment of the invention, the measurement of step g) comprises an electrochemical measurement, such as e.g. an amperometric measurement or a voltammetric measurement.

In an especially preferred embodiment of the invention, the voltammetric measurement is performed using differential pulsed voltammetry or other means for reference signal subtraction to increase the signal to noise ratio.

Preferably, the voltammetric measurement is performed using detection electrodes positioned in the sample chamber. The reference signal may e.g. be retrieved from another chamber remote to the sampling chamber.

Voltammetric detection is preferably performed by means of a 5'-3' exonuclease degradable, oligonucleotide probe, the degradation of said nucleic acid probe resulting in release of a detectable component such as a redox active component.

The redox active component may e.g. be a metallocene such as e.g. ferrocene, which can be measured with high sensitivity and specificity in voltammetric detection scheme. Preferably, the redox active component is a metallocenyl group. More preferably it is a ferrocenyl group. A representitative redox active component for the probe is ferrocenyl and metallocenyl, more advantageously N-substituted ferrocene or metallocene carboxamides. The ferrocene or metallocene ring, which constitutes the labeling moiety, may be un-substituted. The above redox active components as well as additional useful redox active components are known in the art and are e.g. described in WO 03/074 731 and EP 1 481 083, which both are incorporated herein by reference.

In solution, the accumulated digested probe may be distinguished from undigested probe due to its different redox activity; the method therefore further includes the detection of the presence or absence of a probe-specific voltage peak using a detection system based on voltammetric analysis of redox activity.

In yet a preferred embodiment of the invention, the measurement of step g) comprises an optical measurement such as e.g. a fluorescence measurement or a measurement of chemiluminescence. The use of optical measurement may require the sample chamber, e.g. the sample chamber of the chip, comprises an window that is transparent for the relevant wavelengths.

A number of different, well-described fluorescence techniques exist. For example, the fluorescence measurement may employ so called TaqMan® which e.g. is describe in U.S. Pat. No. 5,723,591.

An aspect of the present relates to a method of detection of biological particles, e.g. excluding spores, the method comprises the step a), b), c), d), f), g) as described herein and a substitute step e1) which replaces step e). Substitute step e1) comprises extracting biological material from the biological particles by heat treating reaction mixture at a temperature in the range of 80° C.-105° C., such as 90° C.-100° C. The duration of the heat treatment is typically in the range of 5 seconds-3 hours, such as 5 minutes-60 minutes.

Another aspect of the invention relates to a method of extracting biological material from biological particles, the method comprising the above steps a), b), c), d), e), and f) as described herein.

Yet a further aspect of the invention relates to a chip for detecting a biological particle from a gaseous sample, the chip comprising a sample chamber, e.g. comprising a first opening in fluid connection with the surrounding air, and
a second opening to form a fluid connection with a device, the sample chamber comprising a gaseous sample.

The sample chamber, e.g. the sample chamber of the chip, is typically a microscale sample chamber. In an embodiment of the invention, the volume of the sample chamber is at most 500 µL such as at most 400 µL, 300 µL, 200 µL, 100 µL, 50 µL, 25 µL, 15 µL, 10 µL, 5 µL, 4 µL, 3 µL, or at most 2 µL, such as at most 1 µL. For example, the volume of the sample chamber may be at most 500 nL such as at most 400 nL, 300 nL, 200 nL, 100 nL, 50 nL, 25 nL, 15 nL, 10 nL, 5 nL, 4 nL, 3 nL, or at most 2 nL, such as at most 1 nL.

Typically, the volume of the sample chamber is at least 10 nL. In a preferred embodiment of the invention, the volume of the sample chamber is in the range of 1 µL-50 µL, such as 5 µL-30 µL.

In an embodiment of the invention, the smallest distance between a pair of opposing walls is at most 20 mm, such as at most 15 mm, 10 mm, 8 mm, 6 mm, 4 mm, 3 mm, or 2 mm, such as at most 1 mm. For example, the smallest distance between a pair of opposing walls is at most 800 µm such as at most 600 µm, 500 µm, 400 µm, 300 µm, 200 µm, 100 µm, 50 µm, 25 µm, 15 µm, 10 µm, 5 µm, 4 µm, 3 µm, or at most 2 µm, such as at most 1 µm.

Typically, the smallest distance between a pair of opposing walls is at least 5 µm. In a preferred embodiment of the invention, the smallest distance between a pair of opposing walls is the range of 50 µm-500 µm, such as 100 µm-400 µm, and 150 µm-350 µm.

In an embodiment of the invention, the length of the sample chamber, e.g. the sample chamber of the chip, is in the range of 1 mm-50 mm, such is in the range of 1 mm-10 mm, 10 mm-20 mm, 20 mm-30 mm, 30 mm-40 mm, or 40 mm-50 mm. In a preferred embodiment the length of the sample chamber is in the range of 2 mm-8 mm, such as 3 mm-7 mm or 4 mm-6 mm. For example, the length of the sample chamber may be about 4.5 mm.

In an embodiment of the invention, the width of the sample chamber, e.g. the sample chamber of the chip, is in the range of 0.2 mm-10 mm, such is in the range of 0.2 mm-1 mm, 1 mm-3 mm, 3 mm-5 mm, 5 mm-7 mm, or 7 mm-10 mm. In a preferred embodiment the width of the sample chamber is in the range of 0.2 mm-2 mm, such as 0.5 mm-1.5 mm and 0.75 mm-1.25 mm. For example, the width of the sample chamber may be about 1 mm.

In an embodiment of the invention, the height of the sample chamber, e.g. the sample chamber of the chip, is in the range of 50 µm -2 mm, such is in the range of 100 µm-1 mm, 200 µm-900 µm, 300 µm-800 µm, 500 µm-700 mm. In a preferred embodiment the height of the sample chamber is in the range of 100 µm-400 µm, such as 200 µm-300 µm.

In an embodiment of the invention, the length of the sample chamber, e.g. the sample chamber of the chip, is approximately 4.5 mm, the width of the sample chamber is approximately 1 mm and the height of the sample chamber is approximately 300 µm.

In an embodiment of the present invention the chip furthermore comprises a first and a second electrode.

The first and/or the second electrode may have different shapes or dimensions. For example, the first and/or the second electrode may have a substantial form chosen from the group of a sheet, a plate, a disc, a wire, a rod; or any combination thereof.

In a preferred embodiment of the present invention, the first and the second electrode may e.g. be sheet-like electrodes.

In a preferred embodiment of the present invention the first electrode and the second electrode are facing each other. For example, they may be positioned at opposite sides of the sample chamber.

The first electrode and/or the second electrode may e.g. be positioned inside the sample chamber, standing free in the sample chamber or attached to one or more of the wall of the sample chamber.

The first and/or the second electrode(s) may be embedded in the sample chamber wall(s). For example, the first and the second electrode(s) may be embedded in the sample chamber walls. Alternatively, the first and/or the second electrode(s) may be positioned in the outer surface(s) of the chip.

Preferably the first electrode and the second electrode are positioned at opposite sides of the sample chamber.

An electrode, e.g. the first electrode and/or the second electrode may be formed in a number of different materials. Typically, the electrodes are formed in metals or alloys. The first and the second electrode may for example comprise a metal selected from the group consisting of silver, gold, platinum, copper, carbon, iron, graphite, chrome, nickel, cobalt, titanium, mercury or an alloy thereof.

It is also envisioned that an electrode may comprise a conducting liquid and even essentially consist of a conduction liquid. The conducting liquid may e.g. be mercury.

The dimension or/and structure of electrodes typically depend on the dimension and/or structure the sample chamber. The length and width of the electrodes are of the same order of magnitude as the length and width of the sample chamber.

The electrodes can be formed by as little as a coating of a few atom layers of conductive material.

In an embodiment of the invention, an electrode, e.g. the first and/or the second electrode, has a thickness in the range of 0.001 µm-2000 µm, such as 0.001 µm-1 µm, 1 µm-20 µm, 20 µm-200 µm, and 200 µm-2000 µm.

In an embodiment of the invention, the sample chamber of the chip furthermore comprises a set of detection electrodes, e.g. two or three detection electrodes, for the detection of the presence or absence of redox active component, which e.g. may be released from a probe. Two detection electrodes may serve as working electrode and counter electrode, respectively. The set of detection electrodes may furthermore comprise a reference electrode. Typically, the detection electrodes are formed in metals or alloys. The electrodes may for example comprise a material selected from the group consisting of carbon, silver, gold, or platinum. After detection, the electrodes may suffer from film formation on the electrode surface. To permit further detection of digested probe, further sets of detection electrodes can be placed within the sample chamber of the chip.

In an embodiment of the invention, the first and second electrode may be the set of detection electrodes.

In a preferred embodiment of this invention, the chip furthermore comprises a temperature-sensing element, which e.g. could be a thermally sensitive metal-based resistor (a thermistor) with a positive temperature coefficient (PTC) i.e., the thermistor exhibits increasing electrical resistance with increases in environmental temperature and decreasing electrical resistance with decreasing temperature.

The thermistor may e.g. be selected from the group of materials comprising copper, nickel, iron, aluminium, platinum, or alloys hereof.

The thermistor may have different shapes or dimensions. For example, the thermistor may have a substantial form chosen from the group of a sheet, a plate, a disc, a wire, or a rod.

The thermistor may e.g. be a wire-formed electrode.

The heating electrode may have different shapes or dimensions. For example, the heating electrode may have a substantial form chosen from the group of a sheet, a plate, a disc, a wire, or a rod.

In a preferred embodiment of the present invention, the heating electrode may e.g. be a sheet-like electrode. In a preferred embodiment of the present invention the heating electrode may be positioned to enable heating from at least one side of the reaction chamber.

In yet another embodiment, one or more supplementary heating electrodes may be positioned on the opposing sides of the reaction chamber.

The heating electrode is made of electrically conductive material, preferably selected from the group of nickel-chrome (NiCr), iron-chrome-aluminum (FeCrAl), iron-nickel-chrome (FeNiCr) or other heating element alloys.

In a preferred embodiment of the invention, the chip comprises one or more conducting contact pads in electrical contact with the electrodes of the chip. The chip may comprise a conducting contact pad in electrical contact with the first electrode. The chip may comprise a conducting contact pad in electrical contact with the second electrode. The chip may comprise two conducting contact pads in electrical contact with each their end of the heating electrode. The chip may comprise two or three conducting contact pads in electrical contact with each their electrode of the set of detection electrodes.

In FIG. 1, two exemplary chip embodiments are illustrated. In FIG. 1 A) the chip (1) comprises the sample chamber (2) and a first electrode (3) and second electrode (4). The first electrode (3) is attached to the upper part (5) of the chip and the second electrode (4) is attached to the lower part (6) of the chip. Both the first and second electrodes are covered by an electrically insulating layer (7) to prevent unwanted electrolysis of the liquid contents of the sample chamber (2). A heating electrode is embedded in the insulating layer on top of the second electrode. The sample chamber is formed via a spacer part (9), which is sandwiched between the first part (5) and the second part (6) of the chip (1). The set of detection electrodes and the temperature sensing element are not shown in FIG. 1.

The chip may comprise a vast array of different materials. It may for example comprise organic polymers such as plastics, metals and semiconductors such as silicon, glasses and ceramics and so fort.

With respect to FIG. 1, the first and second parts could e.g. comprise materials such as plastics, semiconductors such as silicon, glasses or ceramics. The first and second electrode could e.g. comprise a metal such as gold or copper. The insulating layer could e.g. be a film of $SiO_2$ or polyimide. The heating electrode could e.g. be a NiCr electrode and the spacer layer might e.g. be cast a polydimethylsiloxane (PDMS) elastomer.

In FIG. 1 B) the first and second electrode are not comprised by the chip but may e.g. be comprised by a device for operating the chip.

A chip typically has a thickness in the range of 0.5 mm-50 mm, and preferably in the range of 2 mm-8 mm.

A chip typically has a length or diameter in the range of 10 mm-500 mm, preferably in the range of 40 mm-200 mm.

A chip typically has a width in the range of 5 mm-200 mm, preferably in the range of 20 mm-100 mm.

The chip may comprise just a single sample chamber or it may comprise multiple sample chambers.

An additional aspect of the invention relates to a device for detecting a biological particle from a gaseous sample, the device comprising:

a chip site where a chip is to be located in order be functionally associated with the device, an electrical interface between the device and the chip for applying an alternating electric field between the electrodes of the sample chamber, and a programmable unit comprising a software that effects that the device performs one or more actions selected from the group consisting of:

providing a gaseous sample in sample chamber, applying an first potential to the first electrode and a second potential to the second electrode, thus resulting in a potential difference and an electric field between the first and second electrode, to assist electrostatic collection, in the sample chamber, of a biological particle in the gaseous sample, contacting the collected biological particle with a first liquid reagent, exposing a reaction mixture to an alternating electric field in said sample chamber, said alternating electric field having a sufficient amplitude so as to extract biological material from the biological particle, performing nucleic acid amplification of a target nucleic acid sequence, measuring the presence of the amplified target nucleic acid sequence and/or measuring products resulting from amplification of the target nucleic acid sequence.

According to the present invention, the term "functionally associated" means that the chip is associated to the device, so that the device can perform one or more actions affecting the chip.

In an embodiment of the invention, the chip is functionally associated with the device when the device can affect the electric field of the contents of the sample chamber.

In an embodiment of the invention, the chip is functionally associated with the device when the device can control the potential of at least one electrode of the chip. For example, the device may be functionally associated with the chip when the device can control the potential of the first electrode and/or the second electrode of the chip.

Being functionally associated may furthermore include that the sample chamber of the chip is in fluid communication with a flow controlling means.

In an embodiment of the invention, the device comprises the first and second electrode, and when the chip is functionally associated the electrical field between the first and second electrode assist collecting the biological particles of the gaseous sample in the sample chamber. In this embodiment, the chip need not comprise the first and second electrode.

The device may also comprise a first reagent chamber for receiving and/or holding a first liquid reagent. Typically, the first reagent chamber has at least one opening, which are in fluid connection with the sample chamber when the chip is functionally associated with the device. Alternatively, the at least one opening of the first reagent chamber is brought in fluid connection with the sample chamber e.g. by using the means for controlling a flow. The first reagent chamber may also be closed by a removable barrier during storage, said barrier being removed either reversibly or irreversibly when the device is used.

The device may furthermore comprise an electrical power supply for supplying power, e.g. to the flow generating means, and/or to the programmable unit, the first and second electrodes.

In an embodiment of the present invention, the chip is functionally associated with the device via the chip site. The chip site may e.g. comprise a plastic interface serving both as connecting material and as gaskets ensuring tight junctions between chip-ports and device-ports eliminate leakage of air and liquid. The chip site may for example comprise a surface and/or cradle for receiving the chip. Typically the chip site comprises at least one conducting contact pad. Preferably, the chip site comprises at least a conducting contact pad for providing electrical contact with the first electrode of the chip and a conducting contact pad for providing electrical contact with the second electrode of the chip. The programmable unit contains instructions, preferably computer readable e.g. software, adapted to facilitate controlling, monitoring, and/or manipulating of the device prior to operation, under operation, and/or after operation.

The programmable unit preferably comprises at least one computer having one or more computer programs stored within data storage means associated therewith, the computer system being adapted to for controlling the device. The programmable unit may in the context of the present invention be chosen from the non-exhaustive group of: a general purpose computer, a personal computer (PC), a programmable logic control (PLC) unit, a soft programmable logic control (soft-PLC) unit, a hard programmable logic control (hard-PLC) unit, an industrial personal computer, or a dedicated microprocessor.

The present invention also relates to a computer program product being adapted to enable a computer system comprising at least one computer having data storage means associated therewith to control, monitor, and/or manipulate the device prior to operation, under operation, and/or after operation. The present invention further relates to a computer readable medium having stored therein a set of routines for enabling a computer system comprising at least one computer having data storage means associated therewith to control, monitor, and/or manipulate the device prior to operation, under operation, and/or after operation.

The programmable unit for controlling, monitoring, and/or manipulating the device prior to operation, under operation, and/or after operation preferably is preferably adapted for operation under harsh conditions, such as artic climate, tropical climate, and combat environment, in particular combat zones having being subjected to atomic, biological, and/or chemical warfare (ABC-warfare). Preferably, the programmable unit complies with the relevant military specifications for such units.

In an embodiment of the invention, the programmable unit comprising the software furthermore effects that the device checks if the chip is functionally associated with the device.

The programmable unit comprising the software may furthermore effect that the device performs one or more actions, such as e.g. 2, 3, 4, 5 or 6 actions, selected from the group consisting of providing a gaseous sample in sample chamber, applying an first potential to the first electrode and a second potential to the second electrode, thus resulting in a potential difference and an electric field between the first and second electrode, to assist electrostatic collection, in the sample chamber, of a biological particle in the gaseous sample, contacting the collected biological particle with a first liquid reagent, exposing a reaction mixture to an alternating electric field in said sample chamber, said alternating electric field having a sufficient amplitude so as to enable extraction of biological material, performing nucleic acid amplification of a target nucleic acid sequence measuring the presence of the amplified target nucleic acid sequence and/or measuring products resulting from amplification of the target nucleic acid sequence.

The programmable unit comprising the software may e.g. effect that the device provides a gaseous sample in sample chamber by operating a flow generating means for providing a gaseous sample.

The programmable unit comprising the software may e.g. effect that the device applies a first potential to the first electrode and a second potential to the second electrode.

The programmable unit comprising the software may e.g. effect that the device contacts the collected biological particle with a first liquid reagent by operating a flow generating means for providing liquid reagent and/or operating the means for controlling a flow.

The programmable unit comprising the software may e.g. effect that the device exposes the reaction mixture to an alternating electric field in said sample chamber by modulating the potentials of at least two electrodes, e.g. the first and the second electrode as described herein or another set of electrodes dedicated to the alternating electric field.

The programmable unit comprising the software may e.g. effect that the device performs a nucleic acid amplification of a target nucleic acid sequence by operating a heating electrode as described herein.

The programmable unit comprising the software may e.g. effect that the device measures the presence of the amplified target nucleic acid sequence and/or measuring products resulting from amplification of the target nucleic acid sequence by operating the detection electrodes related to differential pulse voltammetry.

In a preferred embodiment of the invention, the device furthermore comprises an electrical interface between the device and the chip for applying an electrostatic field between the first and the electrodes of the sample chamber.

The device may additionally measure a reference signal, i.e. a signal from a sample that either comprising a sample without a biological particle or comprises a well defined amount of a given biological particle. The reference signal may e.g. be retrieved from another chamber remote to the sampling chamber, e.g. a chamber located at another position of the chip, or a chamber located at another chip.

The device may furthermore comprise an internal power supply.

The internal power supply may e.g. comprise a battery. The amount of energy to be utilized during a PCR reaction can be estimated as the amount of heat required to heat a volume of water equivalent to that of the fluid sample between the minimum and maximum temperatures of the PCR cycle. This temperature difference is approximately 50 K, and so the heat to be transferred per cycle is approximately 6 Joules for a 30 µL sample volume. Running for example 60 cycles, the total energy consumption for one PCR reaction amounts to 60*6=360 Joules. Using a ramping time comparable to commercial thermocyclers (i.e. 2° C. per second) the power required is 360*2/50=14.4 W.

The battery voltage is considered to be the rated voltage of the battery, e.g. 1.2V per cell for nickel-cadmium (NiCd) and nickel-metal hydride (NiMH) batteries and 3.6V per cell for most lithium-ion (Li-ion) batteries. The charge capacity of the battery is typically given in terms of milliAmp-hours (mAh) and is called the battery's C-rating. For example, a load current of 1C for a battery with a C-rating of 1200 mA-hours is 1200 mA. A battery can be viewed as being ideal, (i.e., with a constant energy capacity) when draining with a load current below 0.1 C (Linden, D. 1984. Handbook of Batteries and Fuel Cells. New York: McGraw-Hill). Therefore, when delivering a power output of 14.4 W using e.g. a battery delivering 10.8V, the C-rating of this battery should be in the range of 14.4/(10.8*0.1)=13300 mAh to avoid peak power consumption that will dramatically reduce the energy capacity.

To enable this energy consumption and power delivery, and to further ensure true portability, rechargeable batteries are preferred. In a preferred embodiment of the present invention rechargeable batteries are selected from the group consisting of Nickel Metalhydride (NiMH) based batteries and Lithium-ion (Li-ion) based batteries.

Also, the internal power supply may comprise a generator, e.g. a portable generator. A portable power generator can be utilized as external power supply. The portable power generator can be recharged from, or simply consist of, a solar module, a battery charger (e.g. AC or car battery charger), a fuel combusting generator, or similar.

Alternatively, power from an external power supply can be provided to the device, e.g. supplemented with a battery back-up.

In an embodiment of the invention, the device furthermore comprises a flow generating means e.g. for providing a gaseous sample in the sample chamber of the chip and being in fluid connection with the second opening of the sample chamber when the chip is inserted in the device.

The flow generating may comprise a pump such as a piston pump, a membrane pump, or a positive displacement pump.

In an embodiment of the present invention, the pump is able to deliver an appropriate air-flow through the chip during sampling (in the range of 10 mL/min to 500 mL/min) is selected. Preferably, the pump should be selected to fulfil one or more of the following criteria: small size, lightweight, pulsation-free flow, reversible flow of the medium by changing motor polarity, flow volume adjustable by controlling voltage.

In an embodiment of the invention, the flow generating means may comprise an inkjet dispenser for creating small droplets of reagent or a similar micro dispensing device.

In one embodiment of the present invention, the gaseous sample can be provided by a passive flow through the chip. This will demand a velocity difference between the chip and the surrounding air to be sampled. The conditions for this occurrence is fulfilled if the chip is moved through the air, e.g. mounted on an airplane in such a way that the first opening is in fluid connection with the surrounding air, optimally opposing the flight direction. Alternatively, the conditions occur if the air is moving around the chip having no velocity compared to the air, e.g. mounted in an air vent.

In an embodiment of the invention, the device furthermore comprises a means for controlling, e.g. a flow through the sample chamber.

The flow may e.g. be a liquid flow and/or a gas flow.

The means for controlling a flow typically comprises one or more valves. The valves may e.g. be selected from the group consisting of a check valve, a two way valve, a multi position valve and a pinch valve.

The valve may e.g. be a microfabricated valve and in an embodiment the valve is integrated in the chip.

In an embodiment of the present invention, the first reagent liquid can be delivered using the Ink-Jet micro dispensing technology. An Ink-Jet cartridge containing one or more compartments comprising the first liquid reagent or separate components of the first liquid reagent is mounted in such a way that it enables the microdispensing of liquids into the reaction chamber.

In yet another embodiment of the present invention, the first liquid reagent or separate components hereof are encapsulated within sealed envelope being composed of a plastic polymer. The plastic polymer envelope is equipped with a build-in heating electrode, enabling the melting of the plastic polymer by the application of an appropriate electrical current and the subsequent release of the encapsulated liquid into the chip. In yet another embodiment, the release of liquid from the sealed plastic polymer envelope can be achieved by mechanical or physical rupturing of the envelope, e.g. by puncturing the envelope with a sharp object.

In one embodiment of this invention, the device can be equipped with a display enabling a visual readout of the results. The display can be in the format of a light emitting source (a LED, a light bulb or similar), a screen, a digital readout or any combinations of the mentioned. In yet another embodiment of this invention, the readout can be communicated in the form of audio signals.

In a preferred embodiment of this invention, the device comprises a component that allows for wireless communication. Examples of wireless communication are 802.11 Mobile Wireless LAN, cellular, Bluetooth®, GPS, and Ultra Wideband. The communication can be one-way, e.g. transport of data from the device or transport of data to the device, or the communication can be the combination, i.e. two-way. Established communication can further be expanded to inter-device communication, i.e, establishment of an ad-hoc network enabling one device to trigger the initiation of sampling of another device thus facilitating the monitoring of, for example, the progression of an aerosol cloud.

In a preferred embodiment of the invention, the device is a low weight and/or portable device.

In an embodiment of the present invention, the device weighs at most 10 kg, such as at most 8 kg, 6 kg, 4 kg, 3 kg, or 2 kg, such as at most 1 kg. It may even be preferred that the device weighs at most 800 g such as at most 600 g, 500 g, 400 g, 300 g, 200 g, 150 g, 100 g, 80 g, 60 g, 50 g, 40 g, 30 g, 20 g, 10 g, or 5 g, such as at most 1 g.

Typically the device has a total weight in the range of 20 g-1 kg, such as 20 g-50 g, 50 g-100 g, 100 g-250 g, 250 g-500 g or 500 g-1000 g.

Yet a further aspect of the invention relates to a system for detecting a biological particle from a gaseous sample, the system comprising a chip as defined herein functionally associated with a device as defined herein.

In an embodiment of the present invention, the chip and the device of the system are integrated and are not meant to be physically separated from each other. In an embodiment of the invention, the chip and the device of the system are integrated so that they cannot be physically separated from each other without damaging the chip or the device.

In an important embodiment of the present invention, the system is a disposable system, e.g. meant to be used only once.

In another important embodiment the chip of the system is disposable but the device is meant to be reused.

A special aspect of the invention relates to a device which is aimed to monitor airborne infectious diseases and is optimized for monitoring of low aerosol concentrations, with direct implications for surveillance of epidemics. The device consists of three integrated technologies hosted in the same container (volume ranging from 10 nL to 10 mL) allowing sampling of bioaerosols, sample preparation for extraction of genetic material with subsequent amplification of DNA or cDNA. The container is supplied by a common input and output for air and liquid. Initially, air is passed through the container in a stream originating by either overpressure at the input or vacuum at the output. The container is equipped with electrodes facilitating electrostatic precipitation. The electrodes are typically formed as two opposing sheets between which the air is passed. However, other configurations, e.g. a single sheet electrode combined with a single or a set of point electrodes can be used to direct the sampled particles to a given spot in the container. The electrical field between the electrodes measured at the shortest distance is below 1000 V/mm in order to prevent electrical sparking. Bioparticles carrying a natural charge are caught in the electrostatic field and their travel through the container is discontinued and they are directed against the electrodes where they precipitate. The capture mechanism is effective and readily a capture efficiency of 80% or more is achieved. The time for the electrostatic precipitation is easily set by external equipment controlling the voltage on the surface electrodes. The precipitation stops when the voltage is turned off. Once a desired volume of air has been processed through the container, the pumping of air can be stopped and the container can be filled with a liquid containing the reagents for DNA/cDNA amplification.

The collected and concentrated bioparticles can now be exposed for the sample preparation. We have demonstrated that endospores of Gram-positive bacteria, which are known to be extremely resistant to mechanical, chemical, and heat degradation, releases chromosomal and plasmid DNA when exposed to an oscillating electrical field across the container. The DNA release occurs within a few seconds if the frequency is above 10 kHz and a maximum release is achieved around 100 kHz. The effect of the oscillating field is the destruction of the integrity of the spores by either direct membrane breakdown, pore forming in the endospore wall, or sudden osmotic swelling due to biochemical degradation of the spore with concomitant activation of otherwise buffered divalent cations as $Mg^{2+}$ or $Ca^{2+}$. The wall of the endospore of Gram-positive bacteria is the most stable enclosing structure found in bacteria, viruses, or fungi, protecting the organism and allowing it to reside dormant under extreme harsh conditions for decades. The sample preparation technology utilizing an oscillating electrical field is therefore effective in releasing genetic material from bacterial cells and spores. The oscillating field can be induced by the same electrodes used for electrostatic precipitation.

Following the initial electrical sample preparation the sample is exposed to heat and cool cycles by rapidly heating the sample to a denaturing temperature and subsequently cooling it. The temperature cycling mediates further breakdown of cells, spores and especially viruses which are unaffected by the oscillating electrical field releases genetic material. Viruses are generally genetic material embedded in protein structures, which quickly denature at higher temperatures. The rapid temperature oscillations (heating rates>40° C./second and cooling rates>15° C./second) are enabled by designing the container for optimal heat exchange. The thermal design is based upon the relation between the total thermal time constants of the materials compared to the thermal time constant of the water in the container. The overall heat capacity of the surrounding materials of the container and the coupling of these materials to each other and to an externally mounted heat sink are important factors in enabling the rapid temperature oscillations. Heat is supplied through a conductive thin film of e.g. Au or Pt in both the top and bottom of the container and it is important that the liquid forms a flat sheet in between the heaters in order to achieve a rapid heating and cooling.

The thin film is heated by passing current through the conductive material. The temperature is controlled by monitoring a four wired Wheatstone bridge thermo-sensor arrangement, allowing the temperature to be set inside the container with an accuracy of ±0.1° C. The oscillations of the temperature further facilitates amplification of DNA or cDNA if the proper biochemical conditions are present within the container.

The device represents a unique and novel combination of methodologies allowing rapid sampling, sample preparation, and DNA or cDNA single molecule amplification integrated in one device.

The term "Fluid" as used herein refers to any fluid, including air, a gas, or a liquid, including water and an aqueous solution.

A special aspect of the invention relates to a micro scaled device for collecting biological particles, extracting genetic material, and conducting temperature dependent biochemical reactions comprising;

a reaction chamber having an inlet opening providing a gas flow capability between the air to be sampled and the reaction chamber, and an outlet opening providing a gas flow capability between the reaction chamber and the exterior of the reaction chamber, the outlet or inlet being connected to an air-flow producing means for drawing the gaseous sample through the reaction chamber from the inlet opening to the outlet opening; said reaction chamber having a capability for introducing biochemically defined solvents into the chamber, a capability for removing the products of the temperature dependent biochemical reaction from the chamber, and a capability for very fast and accurate control of the temperature of the reaction chamber, and a collecting and electrolyzing component arranged within the reaction chamber between the inlet opening and the outlet opening, said collecting and electrolyzing component consisting of two or more electrodes positioned in parallel and having the surfaces or at least a part of the surfaces coated with or consisting of material capable of leading an electrical current.

In a special embodiment of the invention, the parallel electrodes enable the generation of an electrical field at an angle or perpendicular to the air-flow passing through the device, facilitating particles present in the sampled air to become electrostatically charged and thereby being captured by adhering to either the positively or negatively charged electrode.

In a special embodiment of the invention, the electrodes apply a high frequency alternating electrolyzing field to said captured biological particles after the introducing said biochemically defined solvents.

In a special embodiment of the invention, the solvents comprise reagents that enable conducting a polymerase chain reaction or PCR.

In a special embodiment of the invention, the solvents comprise reagents that enable conducting a ligase chain reaction or LCR.

In a special embodiment of the invention, the solvents comprise reagents that enable conducting a transcription-based amplification.

In a special embodiment of the invention, the solvents comprise reagents that enable conducting a restriction-based amplification.

In a special embodiment of the invention, the reaction chamber is adapted to contain in the range of approximately 0.1 µl to 500 µl of fluid.

In a special embodiment of the invention, the reaction chamber is adapted to contain in the range of approximately 1.0 µl to 5 µl of fluid.

In a special embodiment of the invention, the reaction chamber has approximately the dimensions of 4.5 mm×1 mm×300 µm or proportionally smaller.

In a special embodiment of the invention, the device is reusable and is fabricated from the group of materials consisting of polymers, silica, glass, metals, and ceramics.

In a special embodiment of the invention, the device is disposable and is fabricated from the group of materials consisting of polymers, silica, glass, metals, and ceramics.

In a special embodiment of the invention, the electrodes comprise at least one plate electrode for leading an electrical current thereby creating an electrostatic field.

In a special embodiment of the invention, the electrodes comprise at least one linear electrode for leading an electrical current thereby creating an electrostatic field.

In a special embodiment of the invention, the distance between the electrodes at an angle or perpendicular to the air-flow through the device is between 0.01 mm and 4 mm.

In a special embodiment of the invention, the applied electricostatic field between the electrodes is between 100 V/mm and 1600 V/mm.

In a special embodiment of the invention, the method further comprising performing cell lysis induced by the application of high frequency alternating electrical fields.

In a special embodiment of the invention, the alternating current is applied at frequencies between 8000 and 200,000 Hz.

In a special embodiment of the invention, the applied pulse sequences are between 1 second and 60 seconds.

In a special embodiment of the invention, the device further comprises a means of transmission for reporting the results of said biochemical reaction In a special embodiment of the invention, the means of transmission is by wire connection, by radio link, by infrared transmission, by microwave transmission, by cellular phone, by GSM module, or by computer network.

Another special aspect of the invention relates to a microbial monitoring system comprising devices as described herein, wherein said microbial monitoring system comprises a network of separate devices.

In a special embodiment of the invention, the monitoring network is an integrated network.

In a special embodiment of the invention, the location of a device, e.g. a device in the network, is determined by means of a global positioning system.

In a special embodiment of the invention, the methods constitute a detection or diagnostics assay.

In a special embodiment of the invention, the detection assay comprises a variable or programmable timer determining the frequency of detection assays.

It should be noted that, according to the present invention, embodiments and features described in the context of one of the aspects of the present invention also apply to the other aspects of the invention.

EXAMPLES

Example 1

Exemplary Embodiment of the Preparation of a Chip

The design embodies a container or reaction chamber that has dimensions being (or scaling proportionally to) 4.5 mm×1 mm×300 µm. The proposed device structure follows the essential schematics of the described concept design.

A silicon substrate base is coated with a thermally resistive layer to define the thermal properties of the device. Subsequently, a resistive heater layer with low resistance, lead out tracks, and contact pads is deposited and patterned. The heater is patterned uniformly to heat the base of the channel. Next a dielectric layer is deposited to insulate the heater from subsequent layers. Then a platinum film is deposited, and patterned to provide temperature sensors and electrodes. The temperature sensors are then selectively insulated from the sample. The silicon wafer fabrication is completed by the processing of any layers that are required for bonding and sealing in the channel formation/lid attachment.

The lid is made of glass to give inherent thermal insulation. A platinum electrode film is deposited and patterned. If required it may be insulated, or it may have temperature sensors patterned in it. The patterning steps are essentially a subset of those used in the silicon wafer fabrication. Fluid access ports are then formed in the lid, a range of processes is possible—but this could be essentially conventional machining. Fluid interface components, such as Luer fittings are bonded to these ports at a convenient stage in the assembly flow.

The channel is defined either by etching into the lid prior to the platinum electrode formation. This is readily possible only if the electrodes on the lid are of relatively coarse geometry allowing trivial fabrication of patterns. Alternately, the lid remains a planar component and the channel is formed in a 300 μm thick "spacer" layer, which is bonded to both the silicon base and the glass lid.

Process Layers Step by Step

In this sub-section we define the layer sequence used to build the device. We outline the functional role(s) of the layer in the device and we give several alternatives in how to obtain the device and list advantages/disadvantages of the choices.

Figure 2:
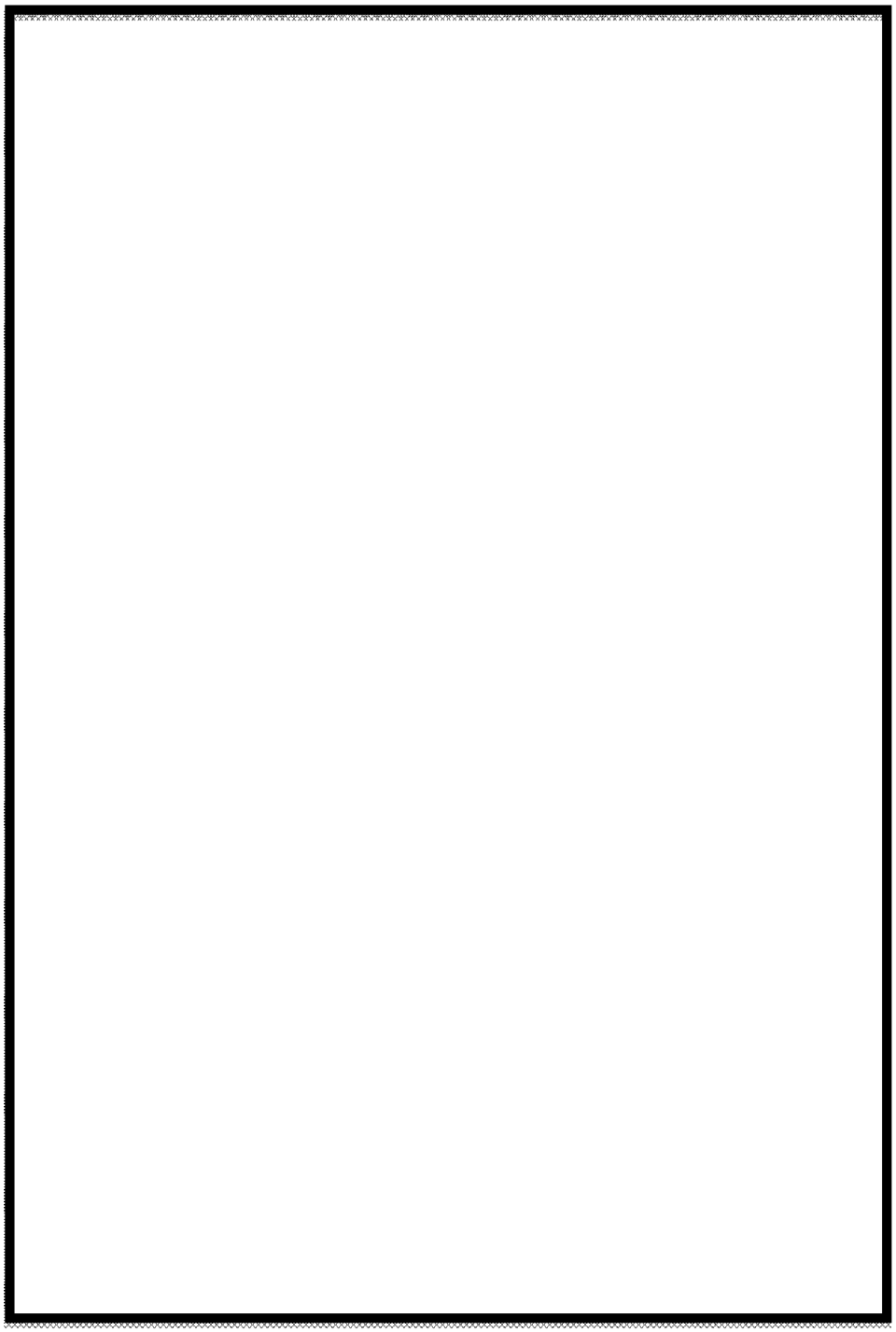
FIG. 2 shows the silicon substrate of Example 1.

Step 1, see FIG. 2

Silicon substrate. This is a silicon wafer in the order of 500 μm thick. A double sided polished wafer is preferable as it facilitates thermal contact to the rear face of the reaction chamber. If lateral thermal isolation can be achieved by a back surface deep RIE process, then either the wafer thickness should be reasonably closely specified or the etch depth varied to compensate for wafer thickness variations. Such wafers are readily available from a large number of sources.

Figure 3:
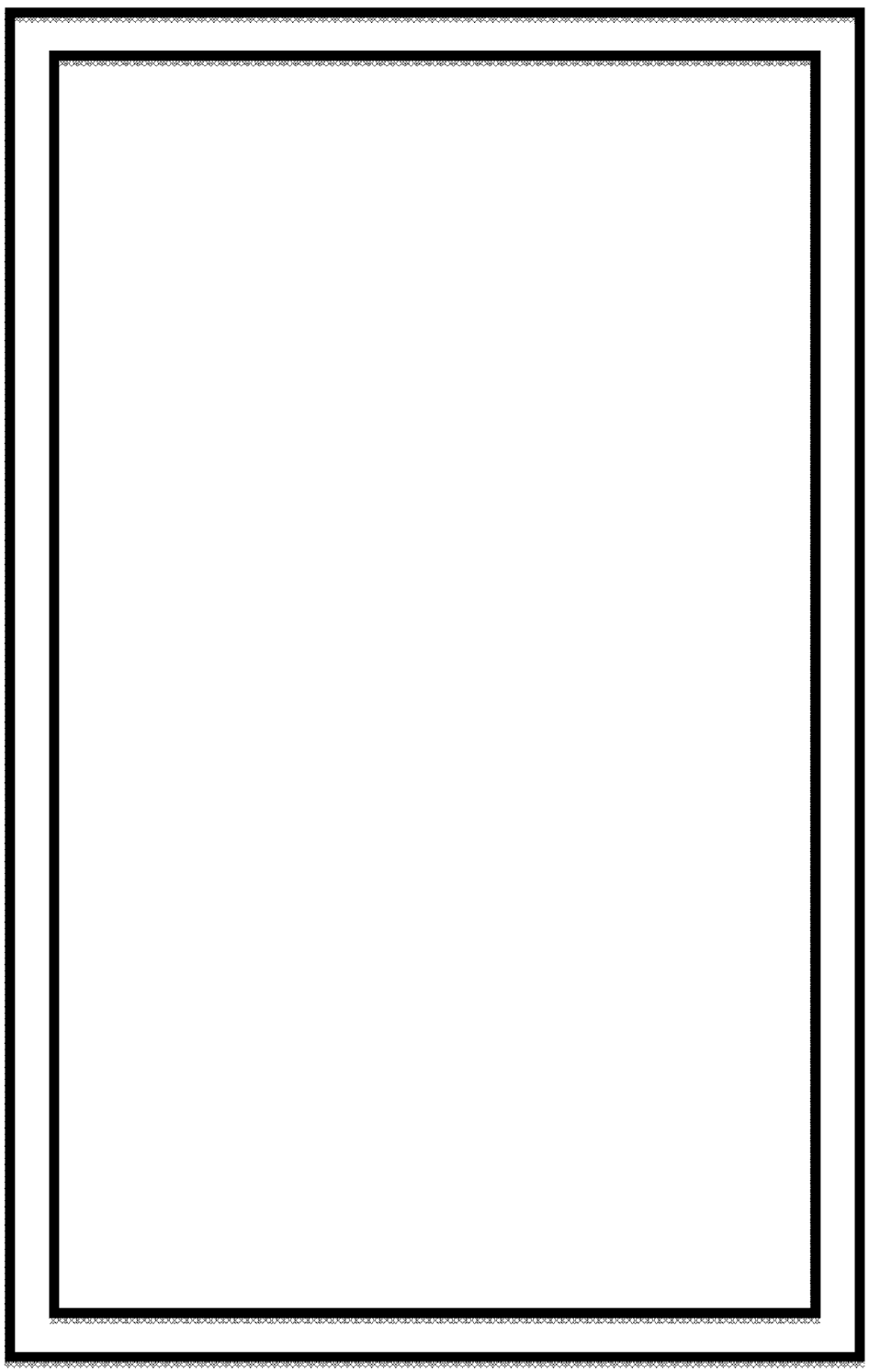
FIG. 3 shows the Thermal insulation layer of Example 1.

Step 2, see FIG. 3

Thermal insulation layer. This layer is deposited on the upper surface of the silicon in order to control the rate of heat loss to the heat sink, and thereby the power required both to maintain the temperature and to heat the sample. For the required PCR cycle times and power levels a polyimide layer of order 20 μm thickness will be required. Various kinds of polyimide are available for use, with BCB (Benzocyclobutene) being an alternate polymeric dielectric material.

Figure 4:
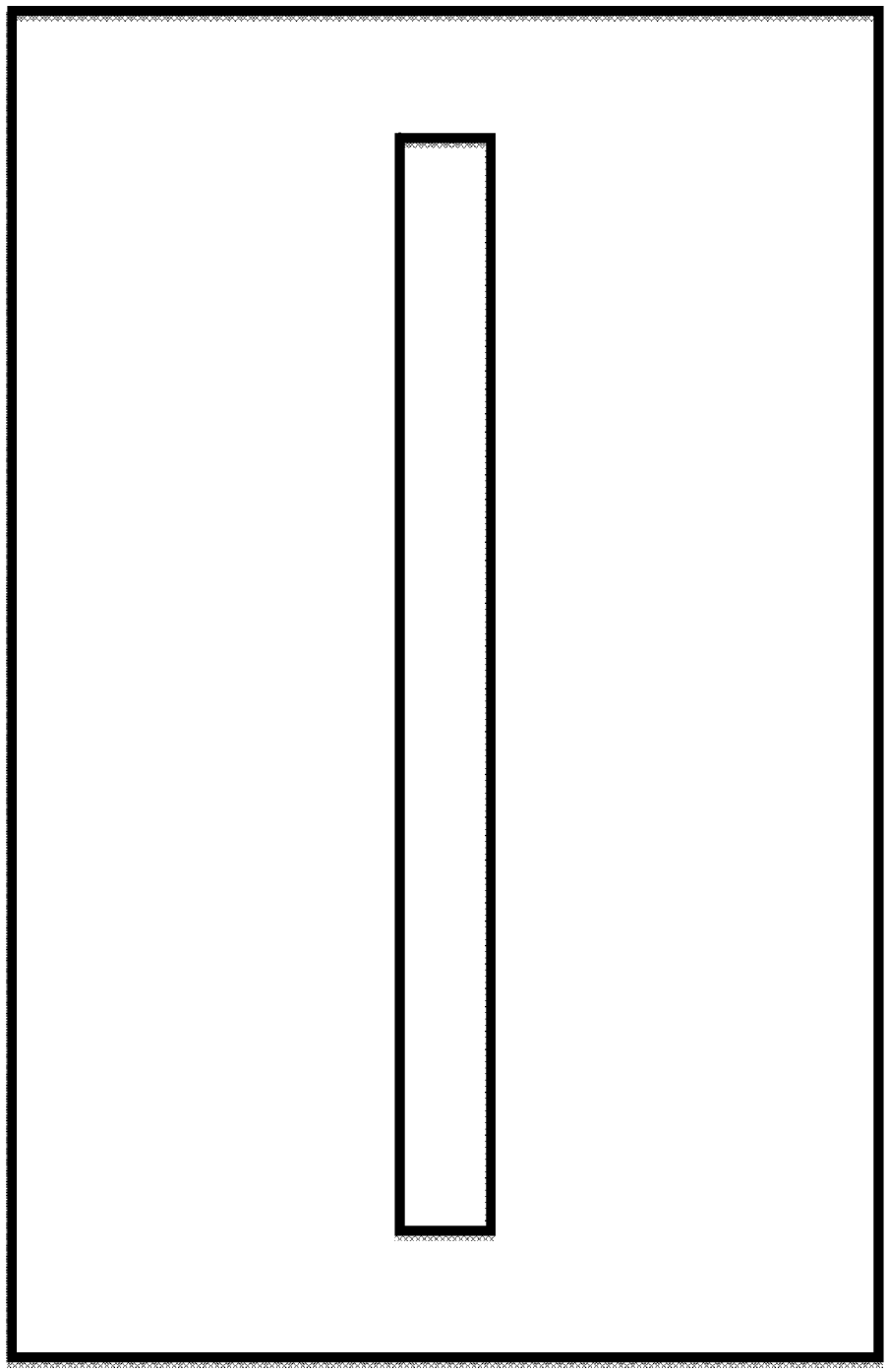
FIG. 4 shows the Heater layer of Example 1.

Step 3, see FIG. 4

Heater layer. This layer is formed in a conveniently resistive material. In the thermal model peak power, dissipation in the heater of order 4 W is indicated. The resistance that it requires depends on the desired drive voltage and current. Currents in the order of 100 mA to 1 A are considered reasonable, with correspondingly voltages ranging from 40 V to 4 V. The required resistance is then in the range of 400Ω down to 4Ω. The heater resistor geometry may conveniently closely follow that of the reaction chamber, being a simple rectangular slab covering the entire base. Thus the resistor is approximately 4.5 squares in length indicating a film resistivity in the approximate range 1-100 Ω/m. This resistivity can readily be achieved with a thin film process. A NiCr resistor can be deposited by sputtering, or evaporation, and patterned by wet etching. NiCr resistor processes meeting the requirement are widely available.

Figure 5:
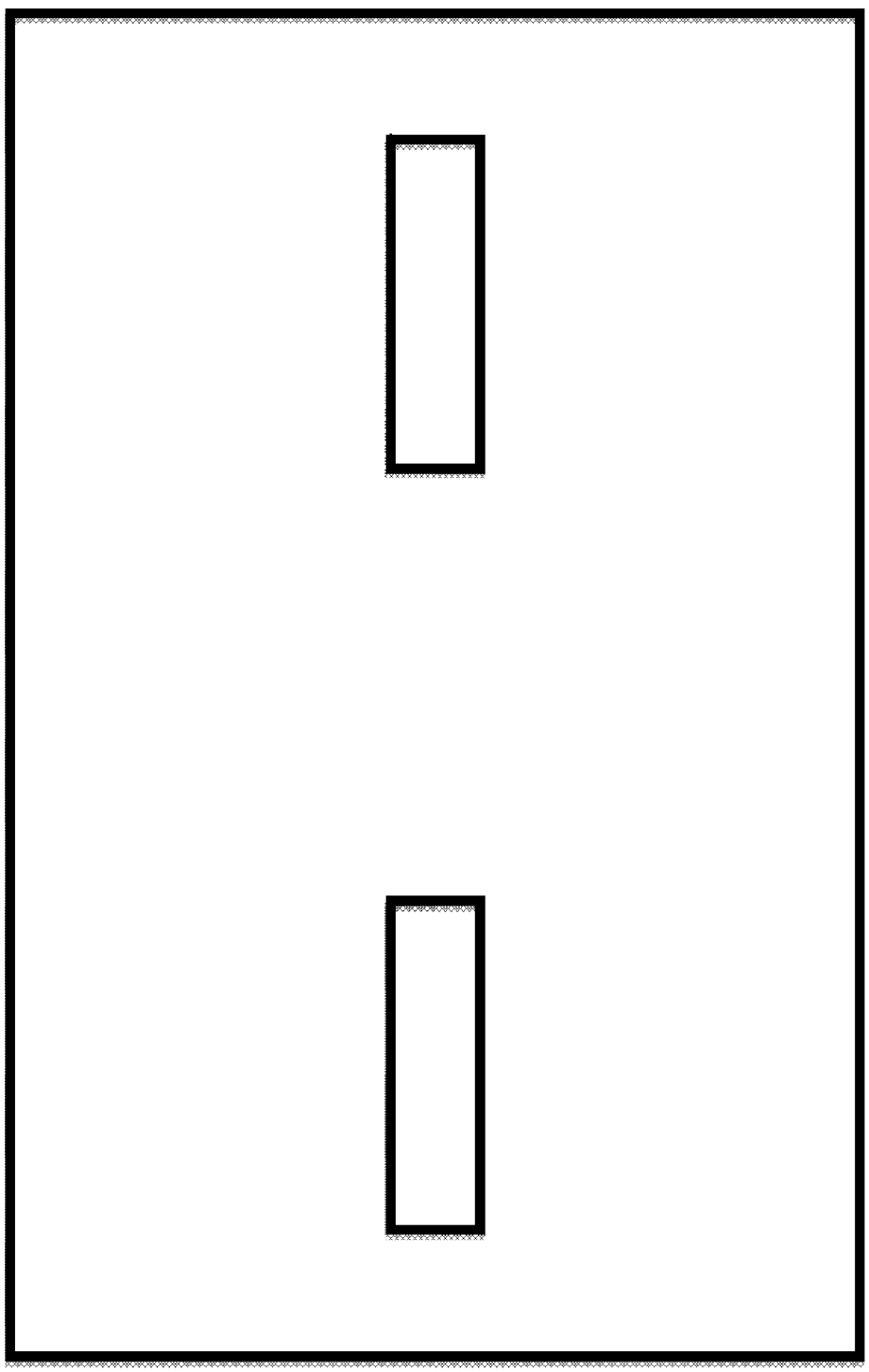
FIG. 5 shows the Contact layer 1 of Example 1.

Step 4, see FIG. 5

Contact layer 1. This layer is deposited immediately following the NiCr deposition and serves to define contacts to the NiCr resistor. Typically this layer would be a thin film of gold. It is defined by wet etching. Self-evidently the pattern is such that there is always NiCr under the gold, but there may not be gold over the NiCr. The typical sequence is a photo-lithographic mask to define a pseudo-layer "gold OR NiCr", etch the gold then the NiCr, remask to define the layer "gold" and re-etch the gold. (There seems essentially no attack on the NiCr film by iodine based gold etchants). Suitable processes are widely available.

Figure 6:
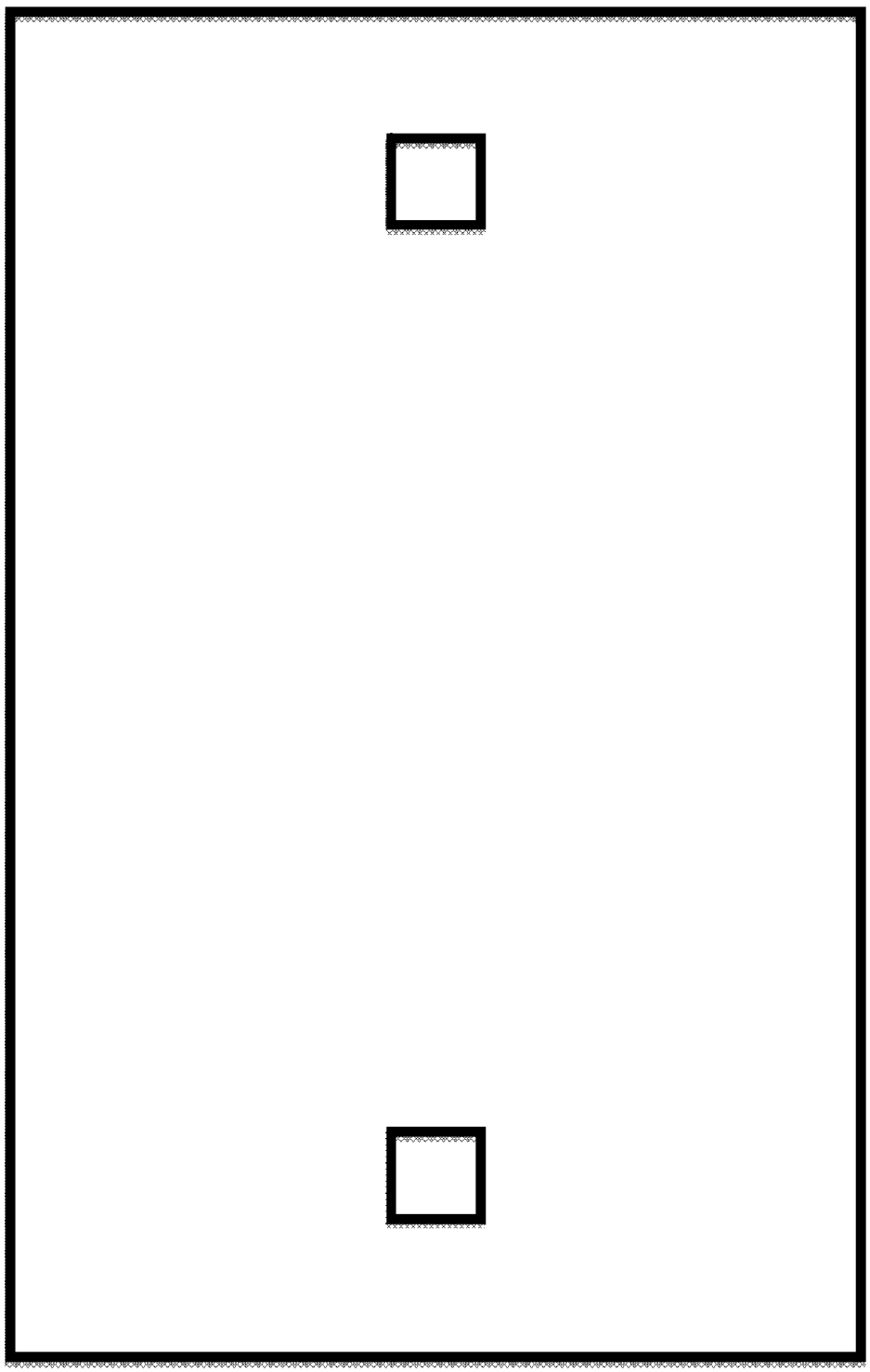
FIG. 6 shows the Electrical insulation layer 1 of Example 1.

Step 5, see FIG. 6

Electrical insulation 1. This layer serves to insulate electrically the heater layer from subsequent conductor layers. The most likely material to be used is a PECVD oxide. The required via/contact openings can be pattered in the oxide using a standard reactive ion etch process. Both the PECVD and RIE processes are widely available.

Figure 7:
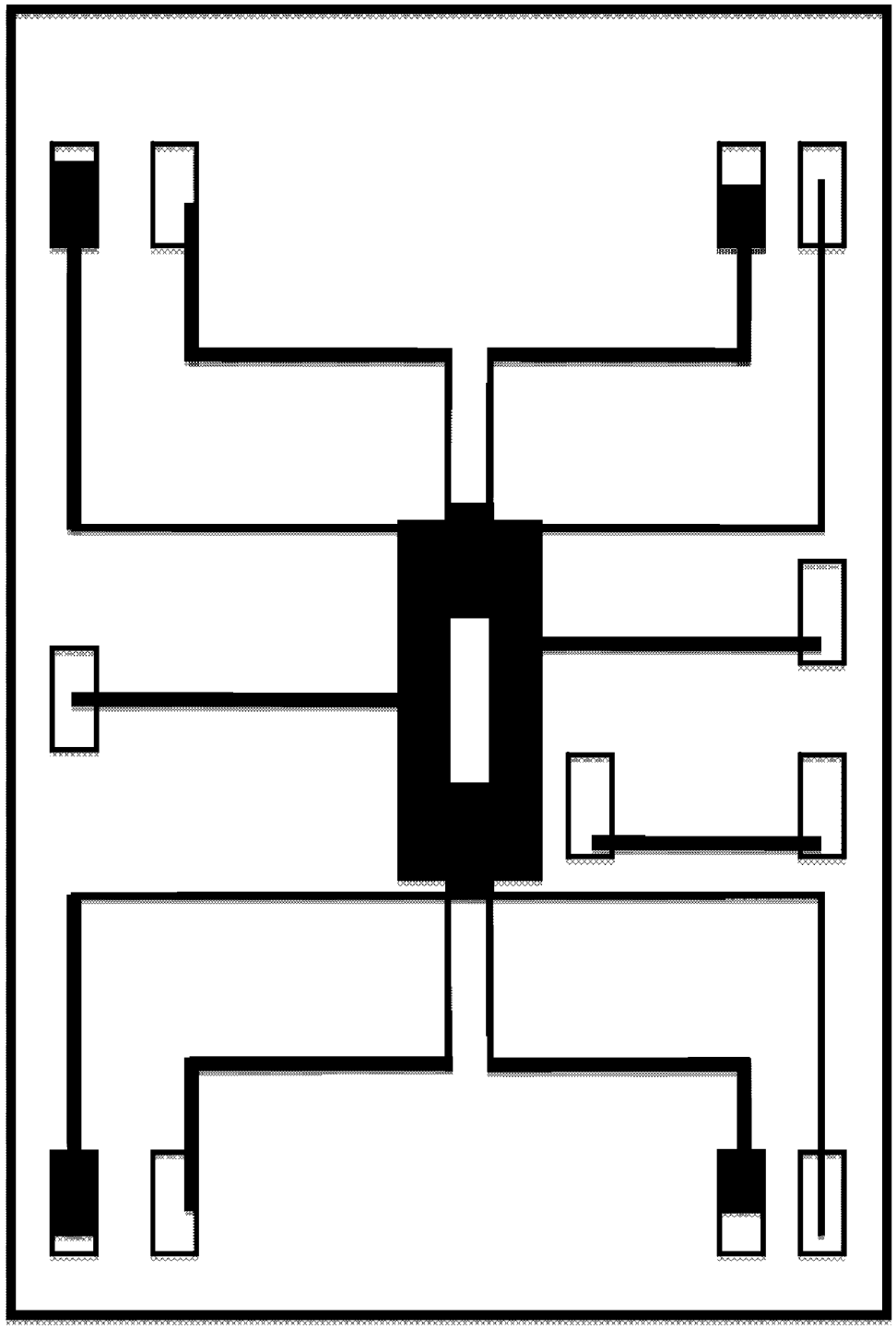
FIG. 7 shows the Platinum layer 1 of Example 1.

Step 6, see FIG. 7

Platinum 1. This layer serves to form both meander structures used as temperature sensors and to form electrodes used in the spore trapping and DNA detection processes. It is envisaged that the film will be patterned by lift-off photolithography and deposited by electron beam deposition. Instead it is possible to use sputter deposition and either sputter back-etching or a reactive ion etch. However, the lift-off route is likely to be the more readily available.

Figure 8:
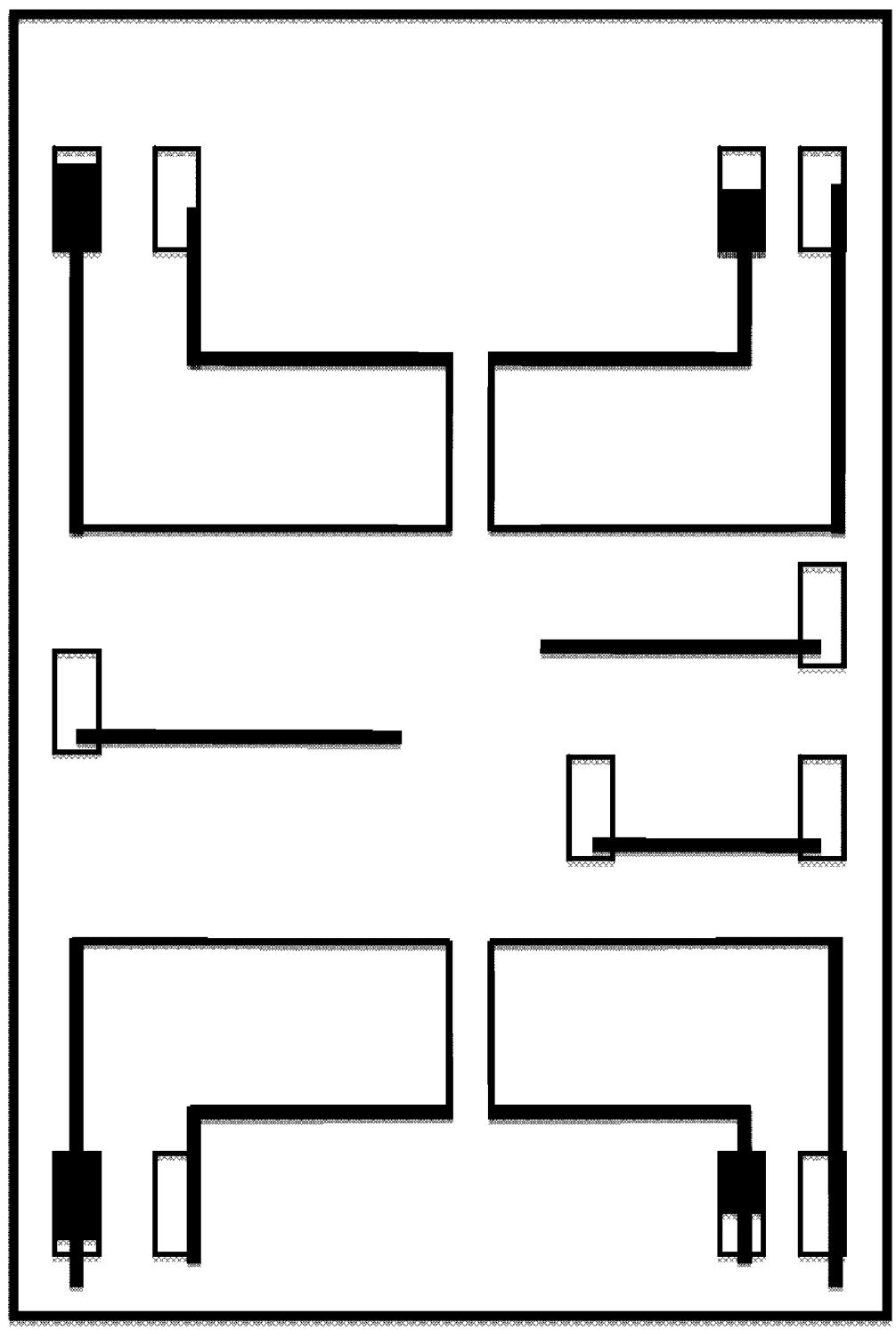
FIG. 8 shows the Contact layer 2 of Example 1.

Step 7, see FIG. 8

Contact 2. A second contact layer material may be required to facilitate wire bonding to the platinum films.

Figure 9:
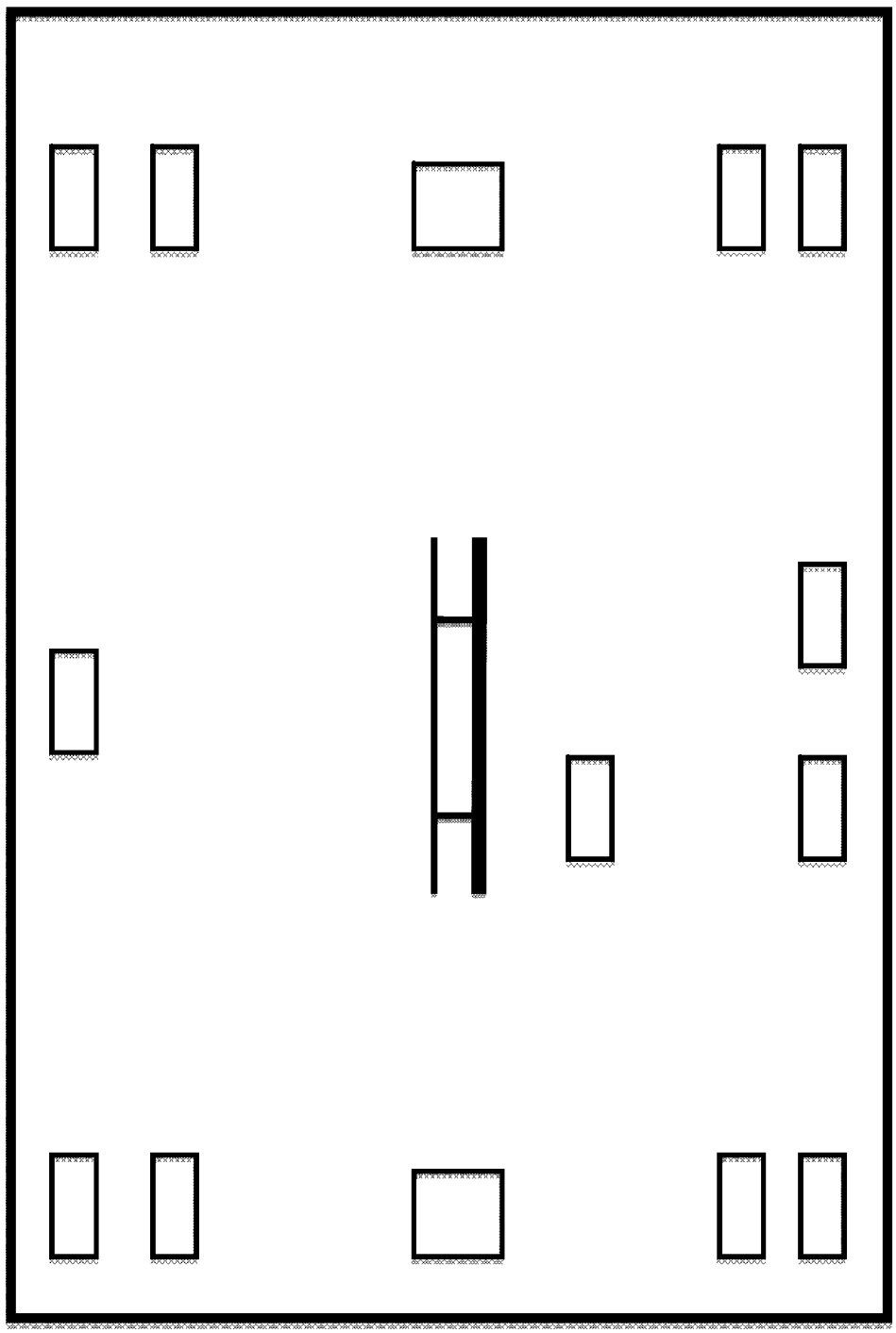
FIG. 9 shows the Electrical insulation layer 2 of Example 1.

Step 8, see FIG. 9

Electrical insulation 2. This layer serves to insulate the temperature sensors from the sample. A PECVD oxide deposited and patterned essentially as step 5 is envisaged.

Figure 10:
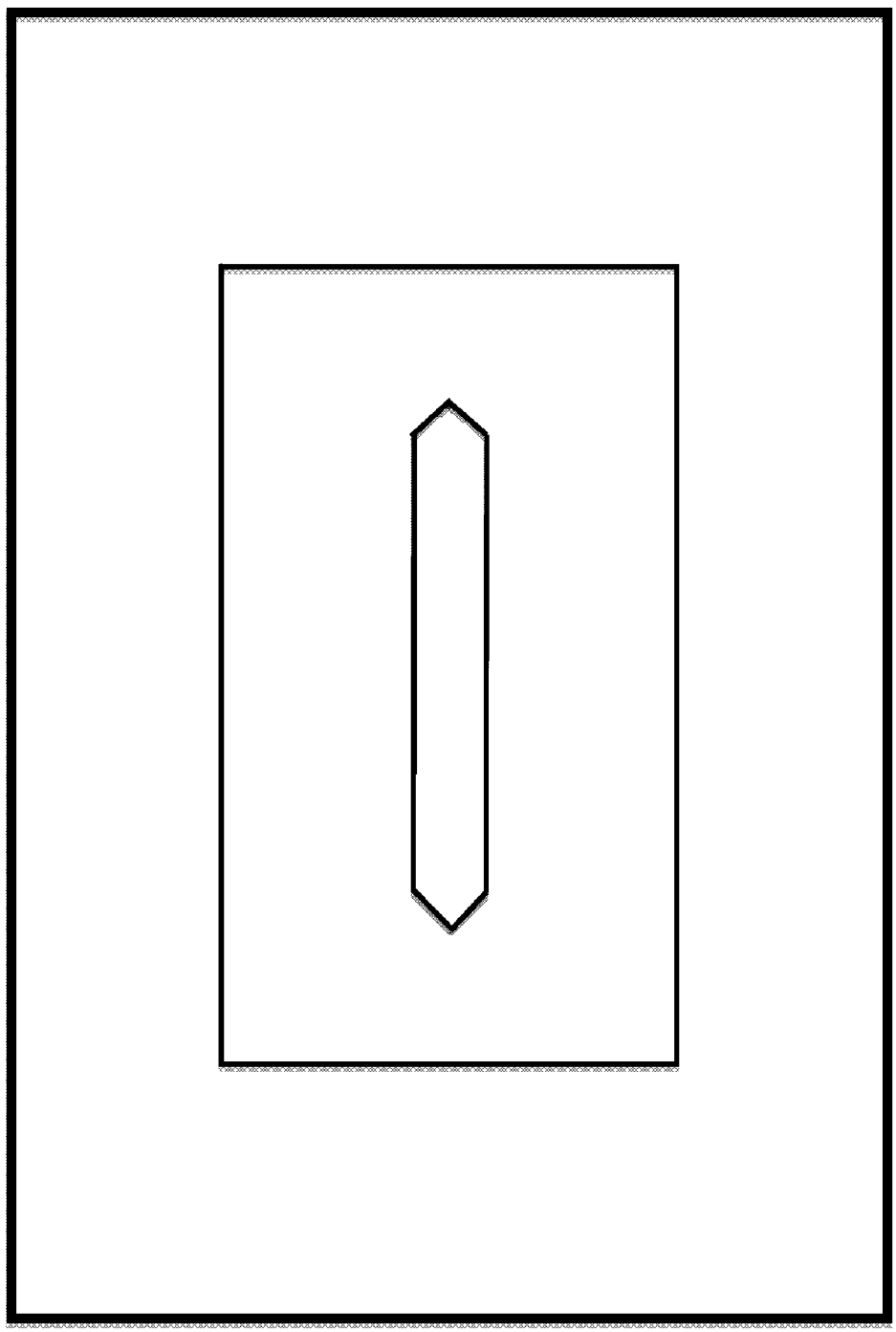
FIG. 10 shows the Planarization 1 of Example 1.

Step 9, see FIG. 10

Planarization 1. If the attachment of the lid requires an especially flat surface then it might be necessary to deposit an overall layer which can be polished to a high degree of flatness, before being removed from everywhere except the lid bonding region. Such planarization processes are increasingly common and are most effective. For example, the liquid crystal on silicon display industry uses processes of this type to allow optical quality mirror surfaces to be formed over dense integrated circuit topography.

Figure 11:
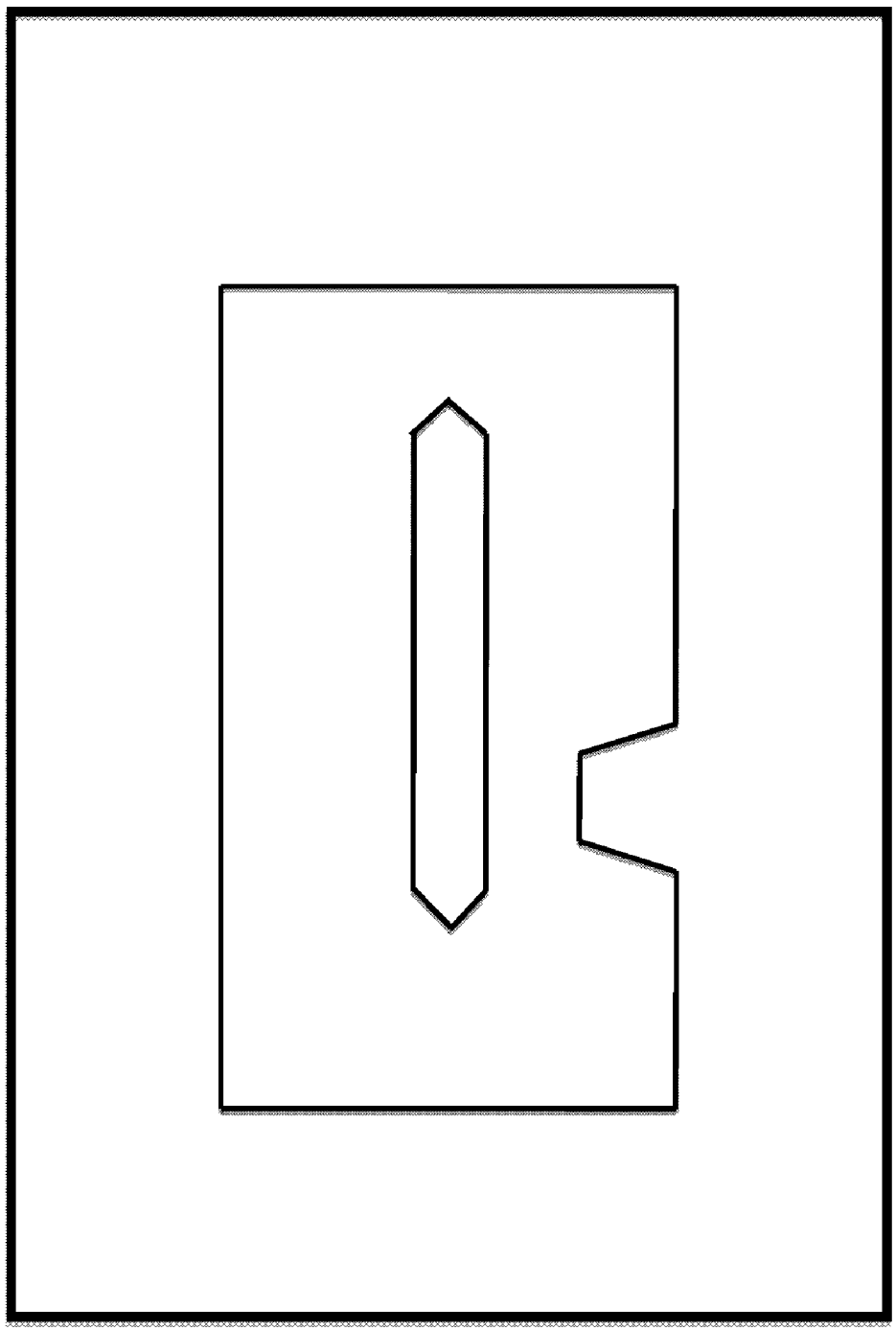
FIG. 11 shows the Spacer of Example 1.
Figure 12:
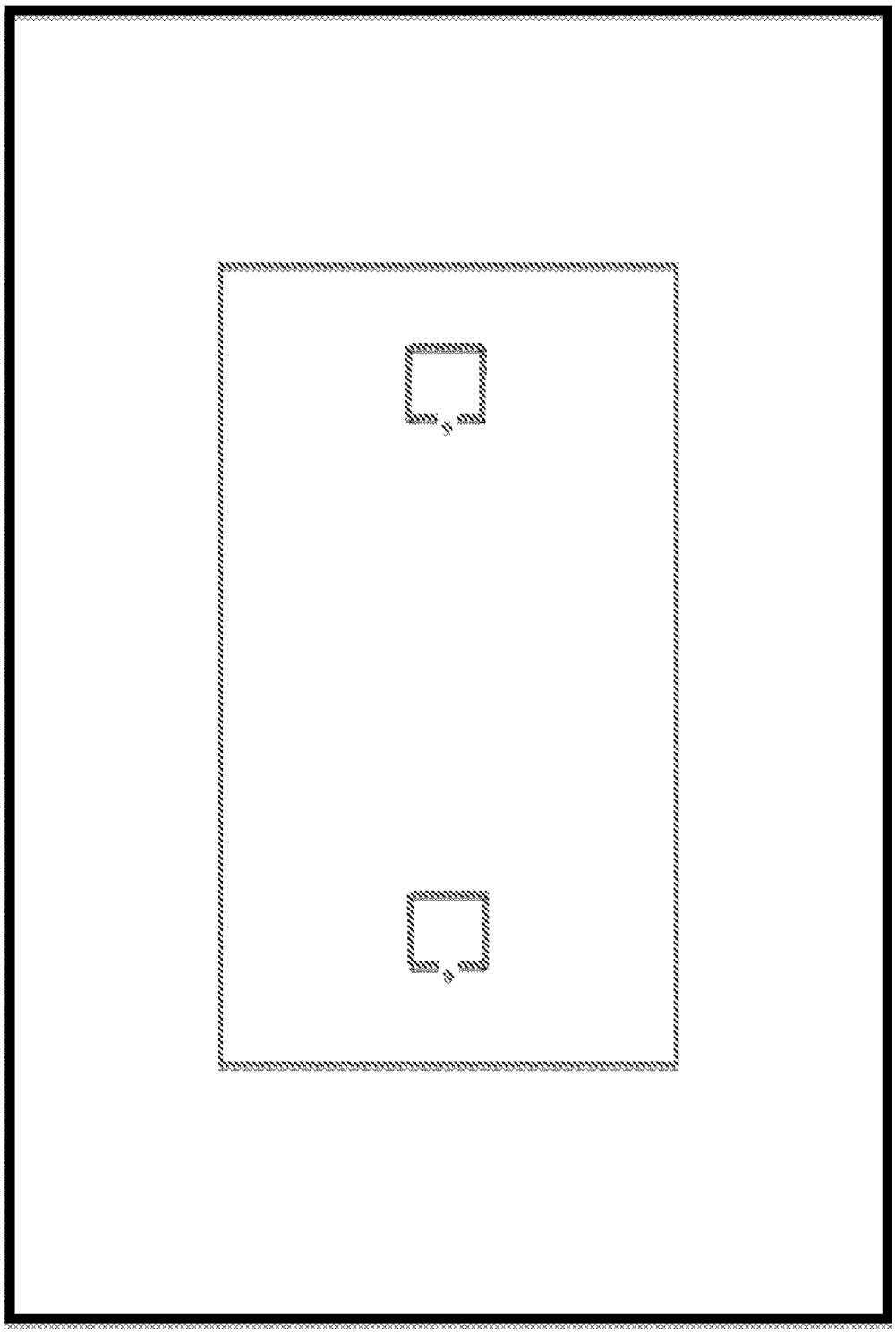
FIG. 12 shows the Lid of Example 1.

Step 10, see FIG. 11 and FIG. 12

For completeness at this stage we show a "picture frame" spacer and the device lid. These are discussed, below. The lid is assumed to have an overall platinum layer or a titanium-gold layer. The notch cut out in the sidewall of the frame is to allow a contact to be brought from the platinum film on the lid down to the main silicon substrate. This is achieved using an injected conductive material, such as a loaded epoxy.

Figure 13:
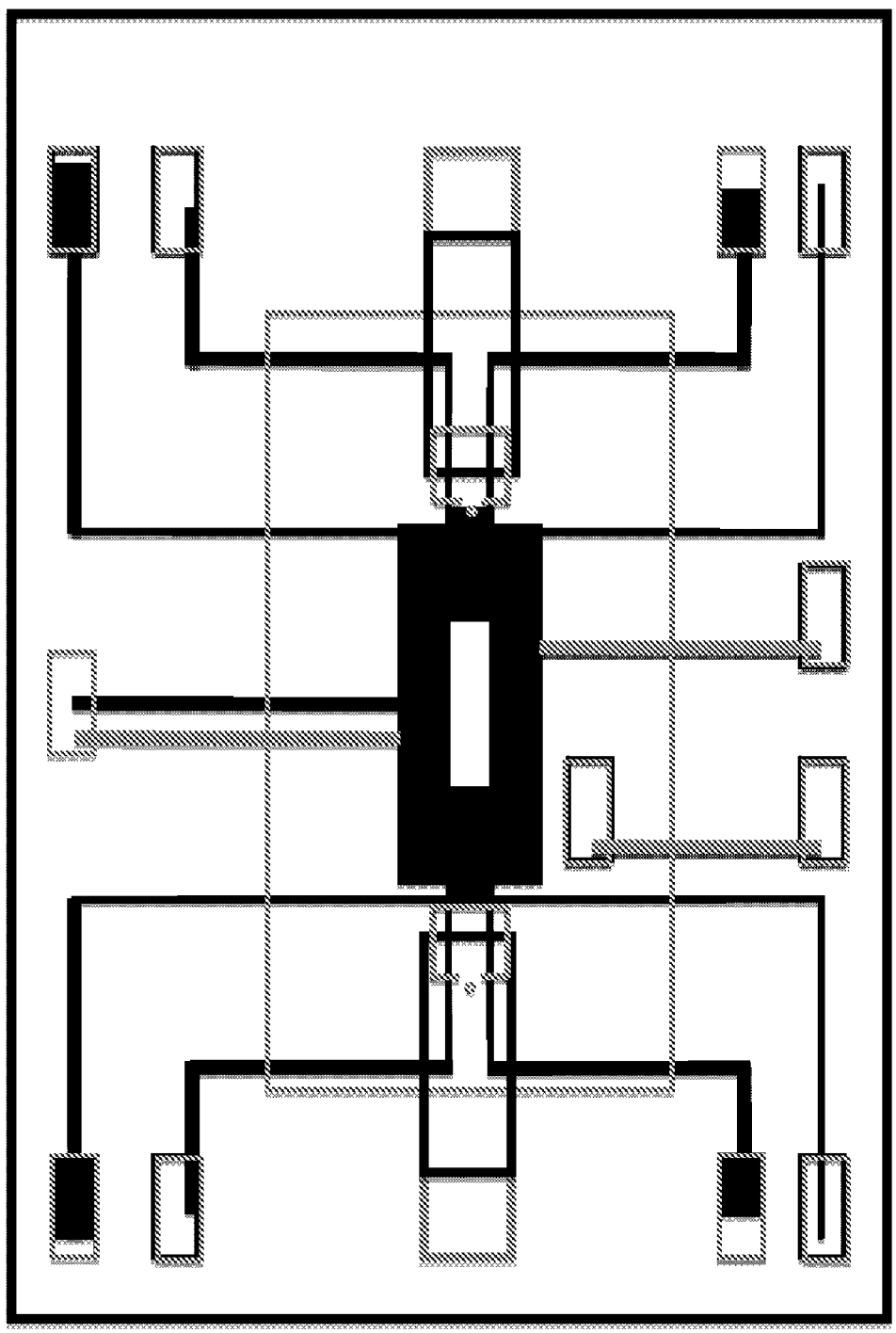
FIG. 13 shows the final chip of Example 1.

The final device is shown in FIG. 13.

Other Process Information

Glass Cover Fabrication

A glass cover is preferred since it offers an effective thermal barrier in a proven material. Slight complexity is introduced by the need to define a platinum structure on this lid, and by the fluid ports, but this is not out of the ordinary.

A key design decision is whether to include any temperature sensing and heating on the cover. If these are included then the process flow is more complicated.

A simple cover having only an exposed platinum electrode used for spore capture could be produced by simply sputtering or electron beam evaporating platinum over the entire glass substrate. If heaters and temperature sensors are incorporated then a process flow selected from steps 3-9 of the base silicon process would be used. There may be little variation in detail of steps of the flow to accommodate the glass as opposed to the silicon substrate.

Once the thin films are fabricated the fluid ports would be machined through the glass. Various means are available for this e.g. using a micro-milling machine with a high speed spindle. Other routes include spark erosion, ultrasonic milling, and sand blasting.

Channel Formation and Device Assembly

The channel is formed using a spacer layer bonded to both the silicon and the glass. Many routes are possible for forming and bonding this layer. Our preferred routes are adhesive films and activated or simply clamped PDMS. The alternatives for channel formation is as follows:

A. Adhesive Bonding

At the simplest possible level it may be possible to define the channel by die, or laser, cutting into a 300 μm thick film adhesive. Such adhesives are widely used in the mass-market for medical assay devices. However, there may be concerns over the long-term reliability for the current application. Using adhesive tape would be possible if the device were used as disposable.

PDMS Molding and Plasma Assisted Bonding

In this process a gasket is moulded in silicone rubber. Such mouldings are readily produced in moderate numbers, with prototypes being cheaply produced. The moulding process allows the retention of very fine detail. The process of bonding silicone rubber to glass by oxygen plasma activation of the silicone is well established in many groups. It readily forms long lasting bonds having high bond strength: typically the silicone rubber material fails, through tearing, before the bond to the glass fails. Since the silicon fabrication completes with a PECVD oxide layer a PDMS gasket can be used to join the two components and form the seal.

If the package and the device are designed together then it may be attractive to use a clamped seal. This would most likely be PDMS. This might be laser, or die, cut from a sheet precision moulded to a thickness marginally in excess of the desired 300 μm. Precision spacers in the assembly would be used to limit the compression of the seal and hence limits lateral excursion in compression.

B. Glass-glass Fusion Bonding

Fusion bonding of glass components is possible provided that both surfaces are very flat and clean. The major qualification over this route is that the temperatures required may prove to be too high to allow the use any polymeric materials in the device.

C. Cold Welding

An interesting possibility is to form a frame defining the channels in thin glass, or perhaps to define the channel by etching into the lid. A thin film metallization is then deposited and pattered to define the sealing area and electroplated with a layer of indium. This layer is of order 25 μm thick, with a similar layer being plated onto the seal region of the other components. To assemble the components the indium is cleaned to remove surface oxide, typically with dilute HCl, and then rinsed with solvents. The two clean indium surfaces are then brought into contact and immediately cold weld together.

Example 2

Method of Determination of Capture Efficiency

Preparation of Standardized Biological Particles

One hundred mg of Biobit *Bacillus thuringiensis* subsp. *kurstaki* containing approximately $10^9$ spores/g (Valent BioSciences Corp, Libertyville, USA) is resuspended in 1 ml of demineralised water and centrifuged for 90 sec. at 12000 rpm. The supernatant is discarded. This procedure is repeated four times. Prior to the last resuspension, a sample is withdrawn for determination of the number of colony forming units (CFU) per ml. The tube is left for exsiccation in e.g. vacuum until dried.

Dilution series is plated on LB-agar plates (Luria Bertani substrate; 10.0 g tryptone, 5.0 g yeast extract, 10.0 g NaCl, 15.0 g agar resuspended in 1.0 liter H2O-pH=7.0, autoclaved), incubated at 30° C. overnight and inspected for visual colonies. The number of CFU enables the determination of spores in the powder.

Measurement of Capture Efficiency

The washed and dried *Bacillus thuringiensis* spores are aerosolized in an appropriate aerosol chamber resulting in an approximate spore concentration of $10^4$-$10^5$ spores per liter. The chip/sampling chamber for which the capture efficiency is to be determined is connected to the device, thus being functionally associated. Then the chip/sampling chamber is connected to the aerosol chamber and aerosol is aspirated through the sample chamber of the chip with a gas flow of approximately 50 mL/minute. A particle counter (e.g. analyzer model 3321 from TSI Inc., 500 Cardigan Road, Shoreview, Minn. 55126-3996, USA) is connected to the outlet of the chip and is counting the number of spores in the size range 1-10 μm that leaves the chip.

First the number of spores of in 25 mL aerosol is measured by aspirating the aerosol while setting the potentials of the first and the second electrode to ground. The measured number of spores is used as the control value, $N_c$.

Then, the selected potentials are applied to the first and the second electrode, another 25 mL aerosol is aspirated through the chip and the number of spores exiting the chip is measured during the aspiration. This value is called $N_s$.

The capture efficiency of the chip/sampling chamber at the selected potentials are calculated as $(N_c-N_s)/N_c*100\%$.

Example 3

Determination of DNA/RNA Release Percentage

One hundred mg of Biobit *Bacillus thuringiensis* subsp. *kurstaki* containing approximately $10^9$ CFU/g (Valent BioSciences Corp, Libertyville, USA) are resuspended in 1 ml of demineralized water and subsequently pasteurised at 70° C. for 5 minutes, subsequently the solution is centrifuged (5000×g, 5 minutes). The supernatant is discarded—This (Tyndalisation) procedure is repeated two times more. The final 1 ml solution contains approximately $10^8$ spores.

This solution is diluted to a final concentration of $10^5$ spores/ml, thus constituting the stock solution.

The sample chamber is filled with a sample of stock solution and the sample is exposed to an alternating electric field having a selected frequency, amplitude, and duration.

To determine the DNA/RNA release percentage of the biological cells of the sample, both the exposed sample and a control containing stock solution is treated with the fluorochrome 4',6-diamidino-2-phenylindole (DAPI). DAPI is widely used as a DNA stain that forms a fluorescent complex when bound to A-T rich sequences in the minor groove of dsDNA. The staining solution is an aqueous solution containing 2.0 μg/ml DAPI.

The sample chamber is eluted with a volume of staining solution which volume is three times the volume of the sample chamber. The eluent from the sample chamber is allowed to incubate at room temperature for 5 minutes.

A volume of control comparable to volume of the exposed sample is stained separately for 5 minutes with a volume of staining solution being approximately three times the volume of the control.

Then an appropriate volume of the control and an appropriate volume of the exposed sample are then viewed in phase-contrast microscopy and fluorescence microscopy (supplied with a DAPI filter). For both the control and the exposed sample, the number of spores is counted by phase-contrast microscopy and the number of spores exhibiting a release chromosomal DNA molecules (visible as blue spots) is counted by fluorescence microscopy. The DNA/RNA release percentage is then determined as $$\frac{d_s}{s_s} \cdot 100\%$$

where $d_s$ is the counted number of blue DNA spots and $s_s$ is the total number of spores.

The background DNA/RNA release percentage may also determined for the control and if it shows an background release of more than 5%, it is suggested that the determination deemed invalid and that it is repeated on a new stock solution of biological cells.

REFERENCES

U.S. Pat. No. 5,723,591
WO 03/074,731
EP 1 481 083
O'Brien et al O'Brien D, Baron P, Willeke K. (1986) Size and concentration measurement of an industrial aerosol. *Am Ind Hyg Assoc J.* 47:386-92
Linden, D. Linden, David. (1984). Handbook of Batteries and Fuel Cells. New York: McGraw-Hill

The invention claimed is:

1. A method for detecting a biological particle from gaseous sample, the method comprising the steps of:
   a) providing a sample chamber and a first and a second electrode, the first and the second electrode and the sample chamber being so positioned that at least a part of the sample chamber is between the first and the second electrode, a distance between the first and the second electrode being at most 20 mm,
   b) providing a gaseous sample in the sample chamber,
   c) applying a first potential to the first electrode and a second potential to the second electrode, thus resulting in a potential difference and an electric field between the first and second electrode, to assist electrostatic collection, in the sample chamber, of a biological particle from the gaseous sample,
   d) contacting the collected biological particle with a first liquid reagent, thus obtaining the reaction mixture,
   e) exposing said reaction mixture to an alternating electric field in said sample chamber, said alternating electric field having a sufficient amplitude so as to enable extraction of biological material from the biological particle,
   f) performing nucleic acid amplification of a target nucleic acid sequence, and
   g) measuring the presence of the amplified target nucleic acid sequence and/or products resulting from amplification of the target nucleic acid sequence.

2. The method according to claim 1 wherein the first and the second electrode are positioned at opposing sides of the sample chamber.

3. The method according to claim 1, wherein the first liquid reagent comprises one or more reagents required to perform a nucleic acid amplification.

4. The method according to claim 1, wherein the first liquid reagent comprises one or more reagents selected form the group consisting of a primer, a triphosphate nucleotide and a polymerase.

5. The method according to claim 1, wherein the first liquid reagent further comprises a 5'-3' exonuclease degradable, oligo-nucleic acid probe, the degradation of said oligo-nucleic acid probe resulting in release of a redox active component.

6. The method according to claim 5, wherein the redox active component is a metallocene.

7. The method according to claim 6, wherein said metallocene is ferrocene.

8. The method according to claim 1, wherein the nucleic acid amplification of step f) is performed using an amplification technique selected from the group consisting of Polymerase Chain Reaction techniques (PCR), Strand Displacement Amplification (SDA), Ligation-Rolling Circle Amplification (L-RCA) and their combinations thereof.

9. The method according to claim 8, wherein the nucleic acid amplification of step f) is PCR.

10. The method according to claim 9, wherein the nucleic acid amplification of step f) is nested PCR.

11. The method of claim 10, wherein said nested PCR is single-tube nested PCR.

12. The method according to claim 1, wherein the measurement of step g) comprises a voltammetric measurement.

13. The method according to claim 12, wherein the voltammetric measurement is performed using differential pulsed voltammetry or other methods for reference signal subtraction to increase the signal to noise ratio.

14. The method according to claim 12, wherein the voltammetric measurement is performed using detection electrodes positioned in the sample chamber.

15. A chip for detecting a biological particle from a gaseous sample, the method comprising:
   a sample chamber with a first opening in fluid connection with the surrounding air and a second opening to form a fluid connection with a device, the sample chamber comprising a gaseous sample,
   a first and a second electrode positioned at opposing sides of the sample chamber,
   a heating electrode,
   a temperature sensing element, and
   a detection electrode.

16. A device for detecting a biological particle from a gaseous sample, the device comprising:
   a chip site where a chip is to be located in order to be functionally associated with the device,
   an electrical interface between the device and the chip for applying an alternating electric field between a first and a second electrode of the chip wherein the first and a second electrode are separated by a distance being at the most 20 mm, and
   a programmable unit comprising a software that effects that the device performs the following:
      providing a gaseous sample in the sample chamber,
      applying a first potential to the first electrode and a second potential to the second electrode, thus resulting in a potential difference and an electric field between the first and second electrode, to assist electrostatic collection, in the sample chamber, of a biological particle in the gaseous sample,
      contacting the collected biological particle with a first liquid reagent,
      exposing a reaction mixture to an alternating electric field in said sample chamber, said alternating electric field having a sufficient amplitude to enable extraction of biological material,
      performing nucleic acid amplification of a target nucleic acid sequence, and measuring the presence of the amplified target nucleic acid sequence and/or measuring products resulting from amplification of the target nucleic acid sequence.

17. A system for detecting a biological particle, the system comprising a chip for detecting a biological particle from a gaseous sample, the chip comprising:
- a sample chamber with a first opening in fluid connection with the surrounding air and a second opening to form a fluid connection with a device, the sample chamber comprising a gaseous sample,
- a first and a second electrode positioned at opposing sides of the sample chamber,
- a heating electrode,
- a temperature sensing element, and
- a detection electrode;
- wherein the chip is functionally associated with a device according to claim 16.

18. The method according to claim 1, further comprising inferring that the biological particle has been detected in the sample if at least the copy of amplified target is present and/or if at least one product resulting from amplification of the target nucleic acid is present.

* * * * *